US009632045B2

(12) United States Patent
Englund et al.

(10) Patent No.: US 9,632,045 B2
(45) Date of Patent: Apr. 25, 2017

(54) SYSTEMS AND METHODS FOR DETERMINISTIC EMITTER SWITCH MICROSCOPY

(71) Applicant: THE TRUSTEES OF COLUMBIA UNIVERSITY IN THE CITY OF NEW YORK, New York, NY (US)

(72) Inventors: Dirk R. Englund, New York, NY (US); Edward H. Chen, New York, NY (US); Ophir Gaathon, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 333 days.

(21) Appl. No.: 14/227,076

(22) Filed: Mar. 27, 2014

(65) Prior Publication Data

US 2016/0161429 A1 Jun. 9, 2016

Related U.S. Application Data

(63) Continuation-in-part of application No. PCT/US2012/060735, filed on Oct. 18, 2012.
(Continued)

(51) Int. Cl.
*G01N 21/64* (2006.01)
*G01N 24/00* (2006.01)
(Continued)

(52) U.S. Cl.
CPC ....... *G01N 24/006* (2013.01); *G01N 21/6402* (2013.01); *G01N 21/6458* (2013.01); *G01N 24/10* (2013.01); *G01R 33/323* (2013.01)

(58) Field of Classification Search
CPC .......... G01N 21/6402; G01N 21/6458; G01N 2201/06113; G01N 24/006
See application file for complete search history.

(56) References Cited

U.S. PATENT DOCUMENTS 3,694,656 A 9/1972 Henning
5,037,376 A 8/1991 Richmond et al.
(Continued)

FOREIGN PATENT DOCUMENTS

WO WO 94/06152 A1 3/1994
WO WO 2008/128051 A2 10/2008
(Continued)

OTHER PUBLICATIONS

U.S. Appl. No. 13/973,499, Jan. 15, 2016 Non-Final Office Action.
(Continued)

*Primary Examiner* — Mark R Gaworecki
(74) *Attorney, Agent, or Firm* — Baker Botts L.L.P.

(57) ABSTRACT

Techniques for deterministic switch microscopy include resolving at least one nitrogen vacancy center in a diamond structure. A magnetic field can be applied across the diamond structure and the nitrogen vacancy centers can be optically excited. The nitrogen vacancy centers can be switched from a dark state to a bright state or a bright state by a dark state by applying at least one microwave pulse. A fluorescent response of each nitrogen vacancy center can be detected and a nitrogen vacancy center can be resolved based on the fluorescent response of each nitrogen vacancy center as it corresponds to the orientation of the nitrogen vacancy center relative to the applied magnetic field.

36 Claims, 14 Drawing Sheets

Related U.S. Application Data

(60) Provisional application No. 61/805,776, filed on Mar. 27, 2013, provisional application No. 61/549,046, filed on Oct. 19, 2011, provisional application No. 61/562,551, filed on Nov. 22, 2011, provisional application No. 61/591,570, filed on Jan. 27, 2012, provisional application No. 61/624,647, filed on Apr. 16, 2012.

(51) Int. Cl.
*G01N 24/10* (2006.01)
*G01R 33/32* (2006.01)

(56) References Cited

U.S. PATENT DOCUMENTS

| | | | |
|---|---|---|---|
| 5,173,761 | A | 12/1992 | Dreifus et al. |
| 5,307,146 | A | 4/1994 | Porter et al. |
| 7,030,704 | B2 | 4/2006 | White |
| 7,166,463 | B2 | 1/2007 | Karpen et al. |
| 7,190,993 | B2 | 3/2007 | Sharma et al. |
| 7,196,782 | B2 | 3/2007 | Fielden et al. |
| 7,619,485 | B2 | 11/2009 | DeNatale et al. |
| 7,655,376 | B2 | 2/2010 | Anderson et al. |
| 7,778,296 | B1 * | 8/2010 | Vuckovic ............... B82Y 20/00 372/41 |
| 7,869,708 | B2 | 1/2011 | Evangelides, Jr. et al. |
| 8,110,898 | B2 | 2/2012 | Lewis et al. |
| 9,385,654 | B2 | 7/2016 | Englund et al. |
| 2003/0052080 | A1 | 3/2003 | Baik et al. |
| 2004/0079280 | A1 | 4/2004 | Lee et al. |
| 2004/0213534 | A9 | 10/2004 | Matsuura et al. |
| 2005/0088248 | A1 | 4/2005 | White |
| 2005/0118349 | A1 | 6/2005 | Whitehead et al. |
| 2005/0152429 | A1 | 7/2005 | Scherer |
| 2006/0134600 | A1 | 6/2006 | Fuhr et al. |
| 2006/0241236 | A1 | 10/2006 | Kuznetsov et al. |
| 2006/0265039 | A1 | 11/2006 | Bartic et al. |
| 2007/0048731 | A1 | 3/2007 | Colicos et al. |
| 2007/0126312 | A1 | 6/2007 | Sung |
| 2007/0216424 | A1 | 9/2007 | Sieh et al. |
| 2008/0096308 | A1 | 4/2008 | Santori et al. |
| 2008/0299565 | A1 | 12/2008 | Schneider et al. |
| 2008/0319290 | A1 | 12/2008 | Mao et al. |
| 2009/0115029 | A1 | 5/2009 | Koyama et al. |
| 2009/0140275 | A1 | 6/2009 | Santori et al. |
| 2009/0171233 | A1 | 7/2009 | Lanfermann et al. |
| 2009/0233445 | A1 | 9/2009 | Lee et al. |
| 2010/0016732 | A1 | 1/2010 | Wells et al. |
| 2010/0084634 | A1 | 4/2010 | Gamo et al. |
| 2010/0135890 | A1 | 6/2010 | Boudou et al. |
| 2010/0140562 | A1 | 6/2010 | Shenderova et al. |
| 2010/0181534 | A1 | 7/2010 | Shenderova et al. |
| 2010/0233820 | A1 | 9/2010 | Pantazis et al. |
| 2010/0298600 | A1 | 11/2010 | Lee |
| 2010/0305309 | A1 | 12/2010 | Ho et al. |
| 2010/0315079 | A1 | 12/2010 | Lukin et al. |
| 2010/0320475 | A1 | 12/2010 | Speck et al. |
| 2010/0328299 | A1 | 12/2010 | Yamazaki et al. |
| 2011/0062957 | A1 | 3/2011 | Fu et al. |
| 2011/0120890 | A1 | 5/2011 | Macpherson et al. |
| 2011/0163291 | A1 * | 7/2011 | Scarsbrook .......... G06N 99/002 257/9 |
| 2011/0177008 | A1 | 7/2011 | Manus et al. |
| 2011/0309265 | A1 | 12/2011 | Babinec et al. |
| 2012/0000415 | A1 | 1/2012 | D'Evelyn et al. |
| 2012/0019242 | A1 | 1/2012 | Hollenberg et al. |
| 2013/0334170 | A1 | 12/2013 | Englund et al. |
| 2014/0100472 | A1 | 4/2014 | Englund et al. |
| 2014/0191139 | A1 | 7/2014 | Englund et al. |
| 2014/0247094 | A1 | 9/2014 | Englund et al. |
| 2015/0192596 | A1 | 7/2015 | Englund et al. |
| 2016/0052789 | A1 | 2/2016 | Gaathon et al. |
| 2016/0077004 | A1 | 3/2016 | Englund |

FOREIGN PATENT DOCUMENTS

| | | |
|---|---|---|
| WO | WO 2010/051580 A1 | 5/2010 |
| WO | WO 2011/102474 A1 | 8/2011 |
| WO | WO 2012/034924 A1 | 3/2012 |
| WO | WO 2013/066446 A1 | 5/2013 |

OTHER PUBLICATIONS

U.S. Appl. No. 13/973,499, Dec. 7, 2015 Amendment and Request for Continued Examination (RCE).
U.S. Appl. No. 14/104,931, Sep. 10, 2015 Non-Final Office Action.
U.S. Appl. No. 14/150,412, Nov. 24, 2015 Issue Fee Payment.
U.S. Appl. No. 14/208,198, Sep. 11, 2015 Non-Final Office Action.
U.S. Appl. No. 14/208,198, Dec. 8, 2015 Applicant Initiated Interview Summary.
U.S. Appl. No. 14/208,198, Dec. 11, 2015 Response to Non-Final Office Action.
U.S. Appl. No. 14/150,412, filed Jan. 8, 2014.
Neumann P., et al., "Excited-state spectroscopy of single NV defects in diamond using optically detected magnetic resonance", *New Journal of Physics*, Institute of Physics Publishing, Bristol, GB, vol. 11, No. 1, 2009, p. 13017-1 to 13017-10, XP020154302.
Steinert S., et al., "High sensitivity magnetic imaging using an array of spins in diamond", *Review of Scientific Instruments*, AIP, Melville, NY, US, vol. 81, No. 4, Apr. 23, 2010, pp. 43705-1 to 43705-5, XP012134958.
Tisler, Julia, et al., "Highly Efficient Fret from a Single Nitrogen-Vacancy Center in Nanodiamonds to a Single Organic Molecule", *ACS Nano*, vol. 5, No. 10, Sep. 7, 2011, pp. 7893-7898, XP055182326.
EP Search Report mailed May 8, 2015 in EP Patent Application No. 12 84 2617.
U.S. Appl. No. 14/208,198, Feb. 12, 2016 Notice of Allowance.
U.S. Appl. No. 14/952,216, Apr. 4, 2016 Final Office Action.
U.S. Appl. No. 14/952,216, Mar. 16, 2016 Response to Non-Final Office Action.
U.S. Appl. No. 14/952,216, Dec. 16, 2015 Non-Final Office Action.
U.S. Appl. No. 13/973,499, Apr. 7, 2015 Response to Non-Final Office Action.
U.S. Appl. No. 13/973,499, Jun. 17, 2015 Final Office Action.
U.S. Appl. No. 14/150,412, Jan. 2, 2015 Non-Final Office Action.
U.S. Appl. No. 14/150,412, Jun. 2, 2015 Response to Non-Final Office Action.
U.S. Appl. No. 14/150,412, Aug. 28, 2015 Notice of Allowance.
Balasubramanian, et al., "Nanoscale imaging manetometry with diamond spins under ambient conditions", *Nature*, vol. 455, No. 7213, Oct. 2, 2008, pp. 648-651, XP055182320.
Manus, et al., "Gd(III)—Nanodiamond Conjugates for MRI Contrast Enhancement", Nano Letters, vol. 10, No. 2, Feb. 10, 2010, pp. 484-489, XP55190250.
McGuinness, et al., "Quantum measurement and orientation tracking of fluorescent nanodiamonds inside living cells", *Nature Nanotechnology*, vol. 6, No. 6, May 8, 2011, pp. 358-363, XP55182222.
Supplementary European Search Report mailed Jun. 22, 2015 in EP Application No. 12846188.
Behr, D. et al., "Lift-off technique of homoepitaxial CVD diamond films by deep implantation and selective etching", Diamond and Related Materials, Elsevier Science Publishers, Amsterdam, NL, vol. 6, No. 5-7, Apr. 1, 1997, pp. 654-657, XP004081116, ISSN: 0925-9635, DOI: 10.1016/S0925-9635(96)00662-0.
Hunn, J.D. et al., "Ion Beam and Laser-Assisted Micromachining of Single-Crystal Diamond", Solid State Technology, Pennwell Corporation, Tulsa, Ok, US, vol. 37, No. 12, Dec. 1, 1994, pp. 57-60, XP000485595, ISSN: 0038-111X.
European Extended Search Report dated Jan. 23, 2015 in EP Application No. 12752171.
U.S. Appl. No. 14/104,931, filed Dec. 12, 2013.
U.S. Appl. No. 14/208,198, filed Mar. 13, 2014.
U.S. Appl. No. 13/973,499, Aug. 24, 2016 Notice of Allowance.
U.S. Appl. No. 13/973,499, Jul. 15, 2016 Response to Non-Final Office Action.

(56) References Cited

OTHER PUBLICATIONS

U.S. Appl. No. 13/973,499, Oct. 8, 2014 Non-Final Office Action.
U.S. Appl. No. 13/973,499, Sep. 15, 2014 Response to Restriction Requirement.
U.S. Appl. No. 13/973,499, Jul. 30, 2104 Restriction Requirement Filed.
U.S. Appl. No. 14/104,931, Apr. 27, 2016 Notice of Abandonment.
U.S. Appl. No. 14/208,198, May 12, 2016 Issue Fee Payment.
U.S. Appl. No. 14/841,922, Aug. 5, 2016 Restriction Requirement Filed.
Aichele et al., "Assembly of Fundamental Photonic Elements from Single Nanodiamonds", 23rd Annual Meeting of the IEEE Photonics Society, Denver, CO, pp. 142-143 (2010).
Boudou et al., "High Yield Fabrication of Fluorescent Nanodiamonds", Nanotechnology, 20:235602 (11 pages) (2009).
Bradac et al., "Observation and Control of Blinking Nitrogen-Vacancy Centres in Discrete Nanodiamonds", Nature Nanotechnology, 5:345-349 (2010).
Catledge et al., "Strong Narrow-Band luminescence from Silicon-Vacancy Color Centers in Spatially Localized Sub-10 nm Nanodiamond", Advanced Science Letters. 4(2):512-515 (2011).
Chang et al., "Mass Production and Dynamic Imaging of Flourescent Nanodiamonds", Nature Nanotechnology, 3:284-287 (2008).
Cheung et al., "Implantable Microscale Neural Interfaces", Biomed Microdevices, 9:923-938 (2007).
DeNatale et al., "Compact, Low-Power Chip-Scale Atomic Clock", Position, Location and Navigation Symposium 2008 IEEE, pp. 67-70 (2008).
Draganski et al., "On the Opto-Electrical Properties of Ion-Implanted Single-Crystal Diamond in the Visible and Near-Visible Regime," RMIT University, Mar. 2011, pp. 1-277 [retrieved on Jan. 10, 2012] Retrieved from the internet: URL:http://researchbank.rmit.edu.au/eserv/rmit:160121/Draganski.pdf.
Englund et al., "Deterministic Coupling of a Single Nitrogen Vacancy Center to a Photonic Crystal Cavity", Nano Letters, 10:3922-3926 (2010).
Fu et al., "Characterization and Application of Single Fluorescent Nanodiamonds as Cellular Biomarkers", PNAS, 104(3):727-732 (2007).
Han et al., "Three-Dimensional Stimulate Emission Depletion Microscopy of Nitrogen-Vacancy Centers in Diamond Using Continuous-Wave Light", Nano Letters, 9(9):3323-3329 (2009).
International Search Report and Written Opinion for PCT/US12/042255, dated Sep. 14, 2012.
International Search Report and Written Opinion for PCT/US12/048830, dated Apr. 5, 2013.
International Search Report and Written Opinion for PCT/US12/055555, dated Jan. 23, 2013.
International Search Report and Written Opinion for PCT/US12/060735, dated Jan. 7, 2013.
International Search Report and Written Opinion for PCT/US12/27235, dated Jun. 13, 2012.
International Search Report and Written Opinion for PCT/US13/045631, dated Nov. 14, 2013.
International Search Report and Written Opinion for PCT/US13/045795, dated Nov. 14, 2013.
International Search Report and Written Opinion for PCT/US14/020565, dated Jun. 23, 2014.
Liu et al., "Plasmon-Enhanced Photoluminescence from Bioconjugated Gold Nanoparticle and Nanodiamond Assembly", Applied Physics Letters, 98:153702-153705 (2011).
Maletinsky et al. "A Robust Scanning Diamond Sensor for Nanoscale Imaging with Single Nitrogen-Vacancy Centres", Nature Nanotechnology, 7(5):320-324 (2012).
Manson et al., "Nitrogen-Vacancy Center in Diamond: Model of the Electronic Structure and Associated Dynamics", Physical Review B, 74:104303 (11 pages) (2006).
Petráková V., "Optical Detection of Charged Biomolecules: Towards Novel Drug Delivery Systems," Acta Polytechnica, 51(5):89-93 (2011) Retrieved from the Internet: URL:https://ojs.cvut.cz/ojs/index.php/ap/article/view/1450/1282 [retrieved on Apr. 27, 2016].
Petráková V. et al., "Luminescence of Nanodiamond Driven by Atomic Functionalization: Towards Novel Detection Principles," Advanced Functional Materials, 22(4):812-819 (2012).
Petráková V., "Interactions of nitrogen-vacancy centers with charged surfaces of functionalized nanodiamond particles for the detection of cellular processes," Apr. 17, 2013 Retrieved from the Internet on Apr. 27, 2016: URL: http://www.fbmi.cvut.cz/files/nodes/5223/public/Disertace Petrakova.pdf.
Qing et al., "Nanowire transistor arrays for mapping neural circuits in acute brain slices", PNAS, 107(5):1882-1887 (2010).
Schietinger et al., "Plasmon-Enhanced Single Photon Emission from a Nanoassembled Metal-Diamond Hybrid Structure at Room Temperature", Nano Letters, 9(4):1694-1698 (2009).
Seker et al., "The fabrication of low-impendance nanoporous gold multiple-electrode arrays for neural electrophysiology studies", Nanotechnology, 21(12):125504 (13 pages) (2010).
Shahriar "(QC Theme) Type-Two Quantum Computing in PBG-Based Cavities for Efficient Simulation of lattice Gas Dynamics" Northwestern University. (62 pages) Final Report Apr. 26, 2008.
Smirnov et al. "Aligned Diamond Nano-Wires: Fabrication and Characterization for Advanced Applications in Bio-and Electrochemistry", Diamond and Related Materials 2009 [retrieved on Jun. 3, 2014). Retrieved from the internet: <URL: http://www.soft-hummingbird.com/Proggis/PTD/[2010)%20-%20Smimov"/o20-%20Diamond%20Nanowires%20(drrn).pdf> entire document.
Supplementary European Search Report dated May 24, 2016 in EP Application No. 13805034.
Yamanaka et al., "SAX Microscopy with Fluorescent Nanodiamond Probes for High-Resolution Fluorescence Imaging", Biomedical Optics Express, 2(7):1946-1953 (2011).
Zou et al. "Fabrication of Diamond Nanopillars and Their Arrays", Applied Physics, letters 92, 053105 (2008).

* cited by examiner

Fig. 1a
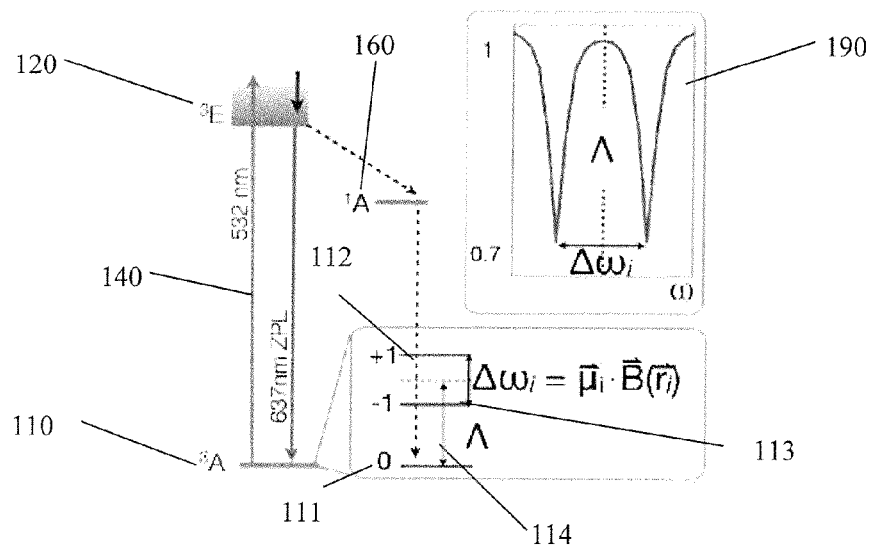
Fig. 1b
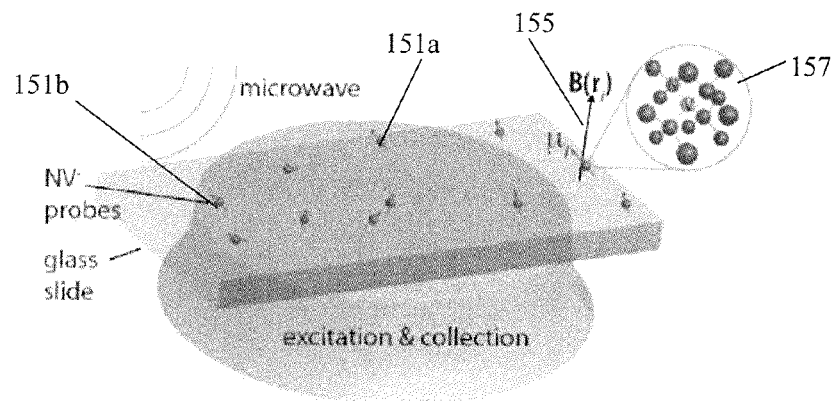
Fig. 1c

SYSTEMS AND METHODS FOR DETERMINISTIC EMITTER SWITCH MICROSCOPY

CROSS-REFERENCE TO RELATED APPLICATIONS

This application claims the benefit of U.S. Provisional Application No. 61/805,776, filed Mar. 27, 2013, and is a continuation-in-part of International Application No. PCT/US2012/060735, filed Oct. 18, 2012, which claims the benefit of U.S. Provisional Application Ser. No. 61/549,046, filed Oct. 19, 2011, U.S. Provisional Application Ser. No. 61/562,551, filed on Nov. 22, 2011, U.S. Provisional Application Ser. No. 61/591,570, filed on Jan. 27, 2012, and U.S. Provisional Application Ser. No. 61/624,647, filed on Apr. 16, 2012, which are each incorporated herein by reference in their entirety and from which priority is claimed.

STATEMENT REGARDING FEDERALLY SPONSORED RESEARCH

This invention was made with government support under Grant Nos. ARO MURI W911NF-12-1-0594, PECASE, and W31P4Q-13-C-0040 awarded by the Army Research Office, Air Force Office of Scientific Research, DARPA SBIR, respectively. The government has certain rights in the invention.

BACKGROUND

The disclosed subject matter relates to techniques for superresolution microscopy, including techniques for deterministic emitter switch microscopy.

In certain conventional far-field optical microscopes, imaging resolution is limited to the diffraction limit, $\lambda/2 (n^*\sin(\theta))$, where $\lambda$ is the illuminating light wavelength, n is the refractive index, and $\theta$ is the collection angle of the imaging optics. Generally speaking, the diffraction limit can be approximately half of the illuminating light's wavelength, or, e.g., approximately 200 nm in the visible spectrum.

In certain instances, it can be desirable to image at resolution below the diffraction limit. For example, as semiconductor device fabrication continues its trend toward increasingly smaller architecture, imaging techniques to resolve and inspect elements smaller than the diffraction limit can be useful for inspection or other purposes. Additionally, imaging for the biological sciences, such as imaging cell structures or certain proteins, can require imaging below the diffraction limit.

Certain techniques for imaging below the diffraction limit can generally be partitioned into two groups: (i) techniques to modify the fluorescence of a cluster of particles around an arbitrarily small area (for example in connection with stimulated emission depletion (STED), reversible saturable optical fluorescence transitions (RESOLFT), or saturated structured illumination microscopy (SSIM)), and (ii) techniques that rely on the stochastic switching of fluorescence molecules to reconstruct the positions of the molecules (for example in connection with stochastic optical reconstruction microscopy (STORM), photoactivated localization microscopy (PALM), or fluorescence photoactivation localization microscopy (FPALM).

However, these techniques can require high excitation power, use of narrow spectrum light sources, particular fluorescent samples, expensive optical detection equipment, and intensive data processing techniques. For example, STED can require an excitation power higher than ~GW/cm$^2$. Moreover, techniques such as STED/RESOLFT can be limited to a small read out area for reasonable acquisition times (e.g., on the order of seconds) due to use of serial scanning imaging techniques rather than wide-field imaging. Techniques that rely on stochastic switching, for example, can require centroid fitting or other statistical processing of readouts over a period of time, which can inherently delay acquisition times due to the stochastic nature of the emitters. Moreover, certain fluorescent biomarkers used in connections with techniques for imaging below the diffraction limit can have brightness approximately an order of magnitude less than 10$^5$ counts/sec, can bleach, blink or degrade during excitation, and/or are toxic to cells.

SUMMARY

The disclosed subject matter provides techniques for deterministic emitter switch microscopy.

In one aspect of the disclosed subject matter, a method for resolving at least one nitrogen vacancy (NV) center includes providing at least one diamond structure with one or more nitrogen vacancy centers within a local location, each being in either a dark state or a bright state. A magnetic field can be applied across the diamond structure. The nitrogen vacancy centers can be optically excited to produce a fluorescent response. A nitrogen vacancy center can be switched from a dark state to a bright state of from the bright state to the dark state by applying at least one microwave pulse to the nitrogen vacancy center, and the fluorescent response of each center can be detected. At least one nitrogen vacancy center can be resolved based on the fluorescent response, the fluorescent response corresponding to the orientation of the nitrogen vacancy center relative to the applied magnetic field.

In one embodiment, optically exciting the nitrogen vacancy center can include directing a continuous wave of pump light at approximately 532 nm to the nitrogen vacancy center. Alternatively, a pulse of pump light at approximately 532 nm can polarize the electron spin of the nitrogen vacancy center prior to applying at least one microwave pulse, and at least a second pulse of pump light at 532 nm can be applied subsequent to application of the at least one microwave pulse to measure the coherence time of the electron spin state. Different pulse combinations can result in measurements of the spin properties; such measurements can include dynamic decoupling techniques.

In one embodiment, a diamond structure can be provided including a plurality of nitrogen vacancy centers, at least some of which having a different orientation relative to the applied magnetic field. A spin sublevel of each nitrogen vacancy center can experience a Zeeman splitting corresponding to the orientation of the nitrogen vacancy center with respect to the magnetic field. A microwave pulse can be applied, e.g., by tuning a first microwave pulse to a field splitting frequency of a first nitrogen vacancy center, which can modulate the fluorescent response of the first nitrogen vacancy center. Additionally, a second microwave pulse that is tuned to a field splitting frequency of at least a second nitrogen vacancy center can also be applied, thus modeling the fluorescent response of the second nitrogen vacancy center.

In one embodiment, a method can include applying a first microwave pulse at a first frequency. The first frequency can be tuned to a field splitting frequency of a first nitrogen vacancy center. A first intensity plot of a first fluorescent response corresponding to the first frequency can be generated. A second microwave pulse can be applied at a second frequency. The second frequency can be tuned to a field splitting frequency of a second nitrogen vacancy center. A second intensity plot of a second fluorescent response corresponding to the second frequency can be generated. A third microwave pulse can be applied at a third frequency. The third frequency can be tuned to a frequency that is not the field splitting frequency of either the first or second nitrogen vacancy center. An intensity plot of a third fluorescent response corresponding to the third frequency can be generated. The position of the nitrogen vacancy center can be resolved by subtracting the first and third intensity plots from the second intensity plot. In certain embodiments, the frequency of microwave emission can be continuously varied.

In one embodiment, the method can further include applying a plurality of microwave pulses and detecting a plurality of fluorescent responses, corresponding to the plurality of microwave pulses, to obtain a full electron spin resonance spectrum for a plurality of locations of a sample. Resolving the nitrogen vacancy center can include fitting the electronic spin resonance spectrum with a sum of Lorentzian dips and generating an intensity map for the nitrogen vacancy center using contrasts from the fitted electron spin resonance spectrum.

In one embodiment, the method can include providing at least one fluorophore having an emission spectrum at least partially overlapping with an emission spectrum of the one or more nitrogen vacancy centers. The fluorescent response of one of the nitrogen vacancy centers can optically excite the fluorophore if the nitrogen vacancy center is within a threshold distance of fluorophore. The fluorescent response of the fluorophore corresponding to the optical excitation of the one of the nitrogen vacancy centers can be detected. The distance of a nitrogen vacancy center from the fluorophore can be determined based on at least the fluorescent response of the nitrogen vacancy center and the fluorescent response of the fluorophore. Furthermore, the orientation of a magnetic dipole of a molecule coupled to the fluorophore can be determined based on at least the fluorescent response of the one of the nitrogen vacancy centers and the fluorescent response of the fluorophore.

In an embodiment, the diamond structure can be exposed to an environment. Two or more microwave pulses, each microwave pulse having a different frequency, can be applied, and a fluorescent response corresponding to each microwave pulse can be detected. Based on the fluorescent response of each nitrogen vacancy center, a characteristic of the environment can be determined. The characteristic can be a local magnetic field, local electric field, or pH of the environment.

A system for resolving at least one nitrogen vacancy center within a focal location using an applied magnetic field is also provided. In an embodiment, the system can include a light source, operatively configured to excite the at least one nitrogen vacancy center in the presence of the applied magnetic field, to induce the nitrogen vacancy center to produce a fluorescent response. A photodetector can be arranged to detect the fluorescent response, if any. A tunable microwave emitter can be arranged to apply at least one microwave pulse to the nitrogen vacancy center. A control unit, coupled to the photodetector and the tunable microwave emitter, can be configured to adjust the frequency of the tunable microwave emitter, and configured to resolve the at least one nitrogen vacancy center based on the fluorescent response, the fluorescent response corresponding to its orientation relative to the magnetic field.

In one embodiment, the photodetector can include an array of pixels, and can be arranged to detect an intensity map of the fluorescent response across the array of pixels. The system can also include far-field optics to direct the fluorescent response to the photodetector. The focal location can include a diffraction-limited area, and the array of pixels can correspond to at least the diffraction-limited area.

In one embodiment, the light source can include a laser adapted to continuously irradiate at least one nitrogen vacancy center with approximately 532 nm light. Alternatively, the light source can be coupled to the control unit, and can include a laser adapted to apply a pulse of pump light at approximately 532 nm to the at least one nitrogen vacancy center prior to application of the at least one microwave pulse, and can be adapted to apply a pulse of pump light at approximately 532 nm to the nitrogen vacancy center subsequent to application of the at least one microwave pulse.

BRIEF DESCRIPTION OF THE DRAWINGS

FIG. 1a is a diagram showing an exemplary nitrogen-vacancy (NV) center in diamond in accordance with an embodiment of the disclosed subject matter.

FIG. 1b illustrates an exemplary sample including a plurality of NV centers in accordance with an embodiment of the disclosed subject matter.

FIG. 1c illustrates an exemplary technique of resolving an NV center in accordance with an embodiment of the disclosed subject matter.

Figure 2:
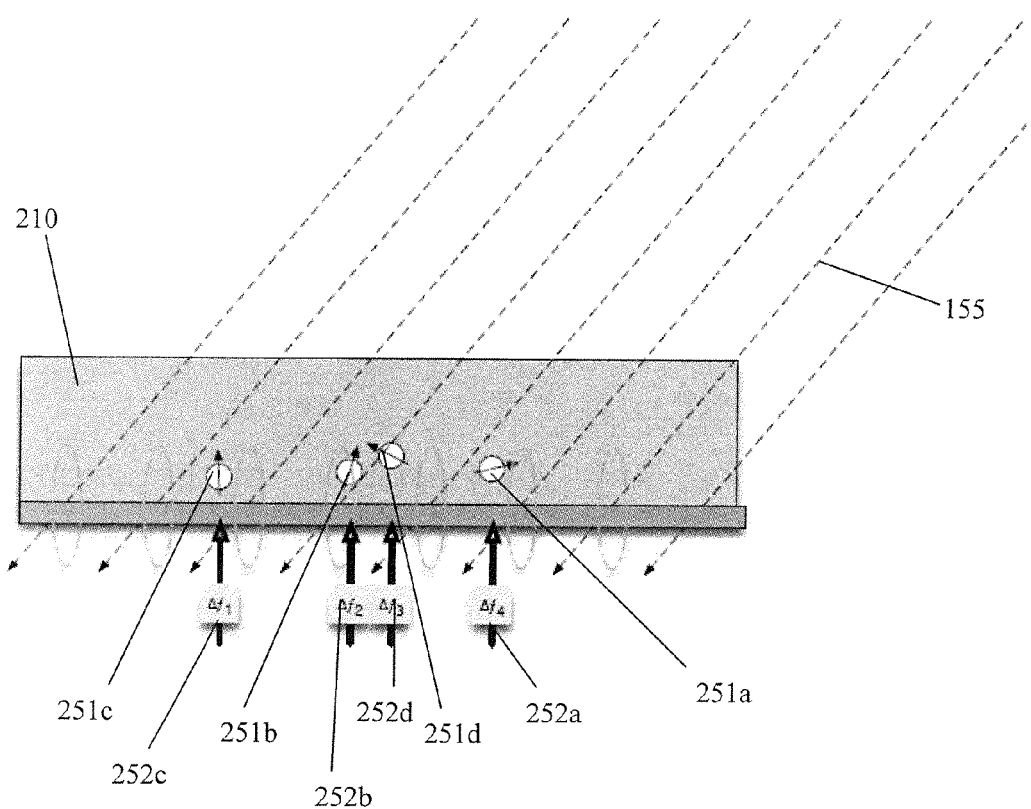
FIG. 2 illustrates an exemplary bulk diamond sample in an applied magnetic field with NV centers having field splitting frequencies corresponding to their alignment relative to the magnetic field in accordance with an embodiment of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the FIGS., it is done so in connection with the illustrative embodiments.

DETAILED DESCRIPTION

Disclosed herein are techniques providing for the deterministic emitter switch microscopy. In one aspect of the disclosed subject matter, a technique for resolving a switchable emitter can include resolving an emitter within a diffraction-limited spot using optically detectable magnetic resonance (ODMR). For purposes of illustration and not limitation, an exemplary deterministic emitter can include the nitrogen-vacancy (NV) center in diamond. As disclosed herein below, a single NV center can be deterministically switched to locate emitters below 30 nm resolutions. Moreover, diamond nanoprobes with the NV can also be photostable. For example, single NV centers can emit without a change in brightness for months or longer. Additionally diamond is chemically inert, cell-compatible, and has surfaces that can be suitable for functionalization with ligands that target biological samples. NV centers can emit in excess of $10^6$ photons per second.

Diamond NV color centers can be formed when a nitrogen atom is substituted for a carbon atom in the carbon lattice, replacing two carbons and creating a physical vacancy with dangling bonds. Diamond NV centers can occur naturally or can be implanted in a diamond structure via ion radiation or the like. The NV− center has an additional electron associated with it, creating a desirable electronic S=1 structure that has a long-lived spin triplet in its ground state that can be probed using optical and microwave excitation. The NV electron spin can act as a sensitive probe of the local environment, and their optical accessibility can allow their use in optically detected magnetic resonance schemes.

Referring to FIG. 1a, a diagram of an exemplary NV center is illustrated. NV centers can absorb photons with a wavelength around 532 nm and emit a fluorescent response, which can be between 637 and 800 nm. A spin-dependent intersystem crossing ($^1A$) 160 between excited state ($^3E$) 120 triplet to a metastable, dark singlet level ($^3A$) 110 can change the integrated fluorescent response for the spin states $|0\rangle$ and $|\pm1\rangle$. The deshelving from the singlet 110 occurs primarily to the $|0\rangle$ spin state, which can provide a means to polarize the NVC.

As depicted in FIG. 1a, transitions from the NV ground state 110 to the excited state 120 are spin-conserving, keeping $m_s$ constant. Such an excitation can be performed using laser light at approximately 532 nm 140; however, other wavelengths can be used, such as blue (480 nm) and yellow (580 nm). While the electronic excitation pathway preserves spin, the relaxation pathways contain non-conserving transitions involving an intersystem crossing (or singlet levels).

Due to the $C_{3v}$ symmetry of the nitrogen defect, the splitting between one "bright" ($m_s=0$) 111 and two "dark" ($m_s=\pm1$) (112 and 113) ground states is given by the crystal field splitting 114. Notwithstanding the effects of an applied magnetic field or certain other factors, the zero field splitting frequency can be approximately equal to 2.87 GHz. The degeneracy of the two dark states can be lifted by an applied magnetic field due to the interaction of the field with the electron magnetic moment, often referred to as the Zeeman effect. The energy difference between the two dark states can be given by $\vec{\mu}, \vec{\beta}$, where B is the magnetic field and $\mu$ is the electron magnetic moment.

A driving field at frequency ω (which can typically be in the microwave range) can induce electron spin resonance (ESR) transitions between the $|0\rangle$ and $|\pm1\rangle$ split states. That is, microwave fields resonant at levels $|0\rangle$ and $|\pm1\rangle$ can perturb the spin populations, and thus the fluorescent response of the NV center. Sweeping over the microwave frequency around the crystal field splitting of the NV center, an electron spin resonance spectrum 190 can be resolved. When excited on either the $m_s=+1$ 112 or $m_s=-1$ 113 resonance, the fluorescence intensity can drop by approximately 30%. That is, applying a microwave pulse at the field splitting frequency corresponding to either the $m_s=+1$ 112 or $m_s=-1$ 113 state can deterministically "switch" an emitter from a bright $m_s=0$ 111 state to a dark $m_s=+1$ 112 or $m_s=-1$ 113 state. Because the energy difference between the $m_s=+1$ 112 or $m_s=-1$ 113 states, and thus the field splitting frequency for each state, can depend via the Zeeman effect on the orientation of the axis of the NV center relative to the applied magnetic field, an NV center with a particular orientation can be uniquely resonantly excited into a dark state, thus providing individual addressability of individual NV centers where a plurality of NV centers have non-overlapping resonances.

Figure 3:
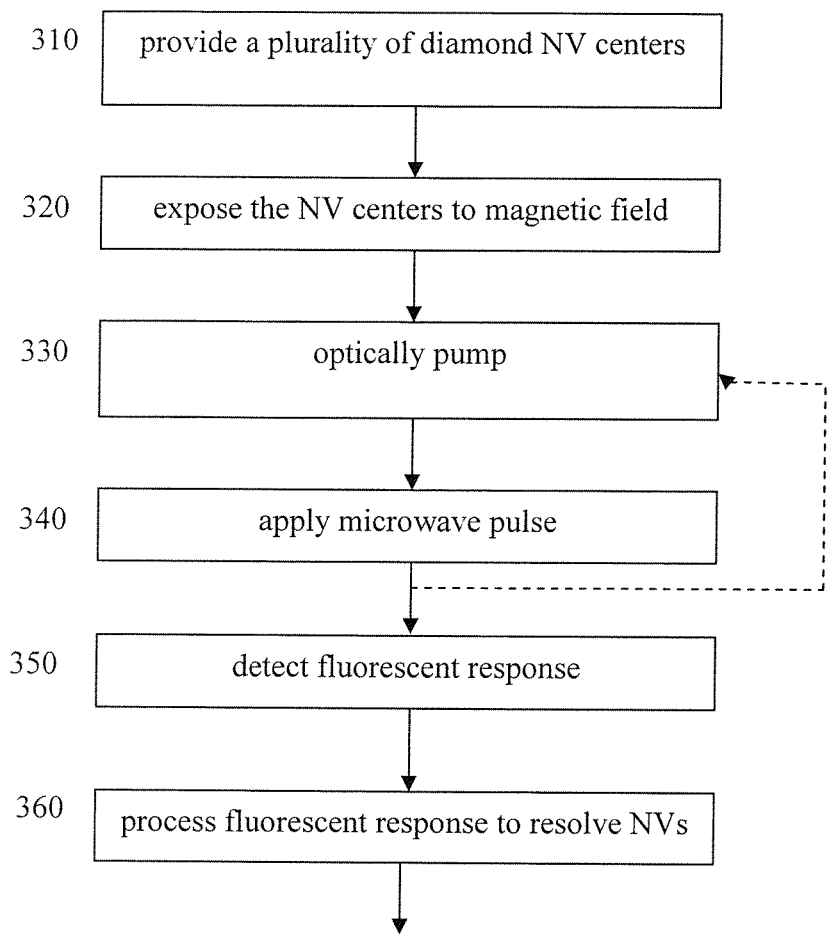
FIG. 3 is a flow diagram illustrating a method for resolving a switchable emitter in accordance with an embodiment of the disclosed subject matter.
Figure 4:
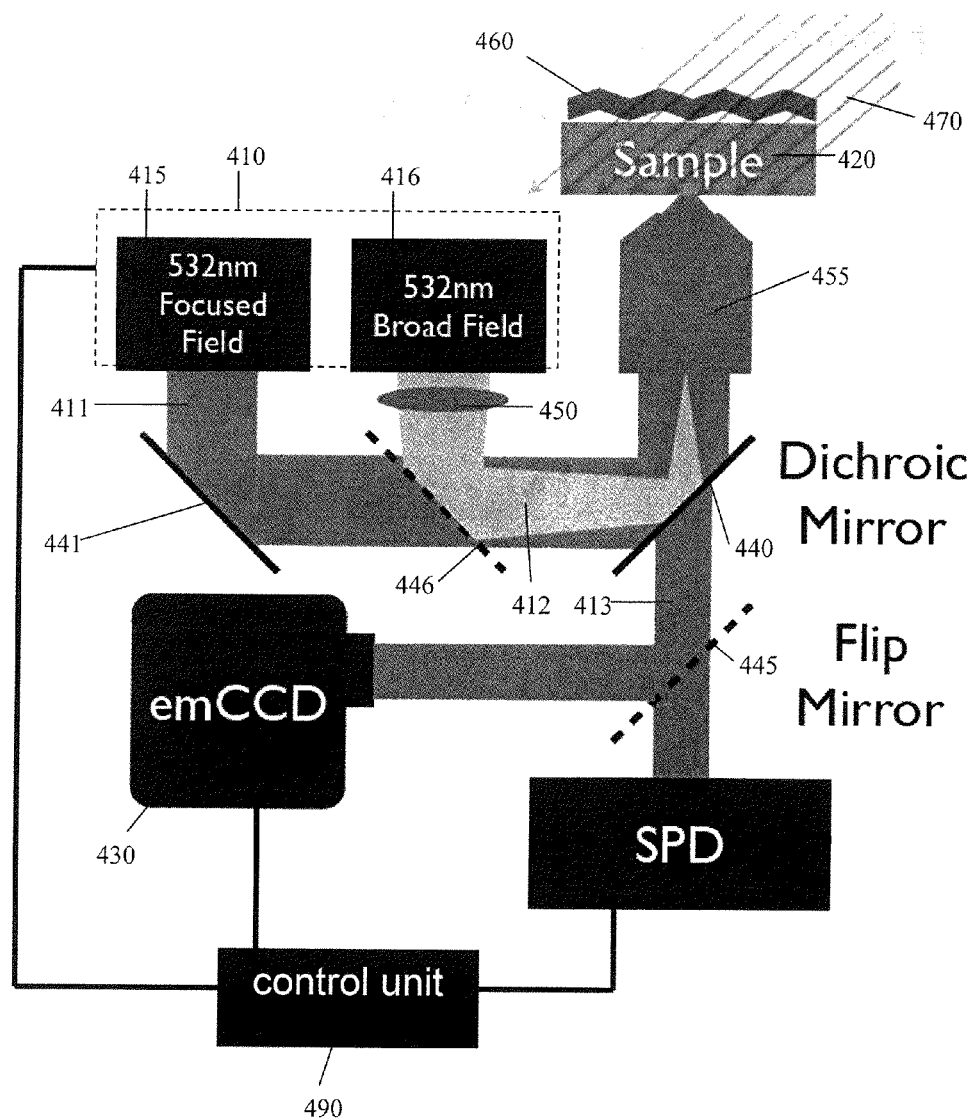
FIG. 4 is a schematic diagram of a system for resolving a switchable emitter in accordance with another embodiment of the disclosed subject matter.

Exemplary embodiments of a method and system for resolving a nitrogen vacancy center will now be described in detail, with reference FIG. 3 and FIG. 4, for purposes of illustration and not limitation.

In an exemplary embodiment, at least one diamond structure with one or more nitrogen vacancy centers can be provided (310), e.g., in a sample 420. For example, the diamond structure can be one or more bulk diamond structures. As noted above, bulk diamond structures can include naturally occurring nitrogen vacancy centers there. Additionally or alternatively, nitrogen vacancy centers can be created in bulk diamond using, e.g., ion implantation techniques. In bulk diamond, the NV centers can have one of four orientations within a single bulk diamond structure, owing to the lattice structure 157 of diamond, depicted for purposes of illustration and not limitation in FIG. 1b. For example, as depicted in FIG. 2, a bulk diamond slab 210 can include NV centers (251a, 251b, 251c, and 251d) with different axial alignment, such that in the presence of a magnetic field 155, each orientation can exhibit a different field splitting frequency (252a, 252b, 252c, and 252d). Alternatively, the at least one diamond structure can include one or more diamond nanocrystals. As with bulk diamond, nitrogen vacancy centers can occur naturally, or can be created using, e.g., ion implantation techniques. FIG. 1b illustrates an exemplary sample 150 with a plurality of NV-probes (151a, 151b, and 151c), for example as included in a plurality of diamond nanocrystals. In certain embodiments, each diamond nanocrystal can include a single NV center. Alternatively, each diamond nanocrystal can include a plurality of NV centers.

A magnetic field 470 (also depicted in FIG. 1b as magnetic field 155) can be applied to at least the NV centers of the diamond structures (i.e., the sample 420 can be exposed (320) to a magnetic field. The magnetic field 470 can be, for example, an applied external magnetic field, and in some embodiments can be substantially uniform. The magnetic field 470 can be created with conventional techniques. For example, the magnetic field 470 can be created by placing a large magnet in proximity to the sample 420 such that the magnetic field created by the magnet is substantially uniform over the sample 420. Additionally or alternatively, the magnetic field 470 can be created by arranging current-carrying coils around the sample 420 to create a magnetic field. In certain embodiments, shielding can be used to eliminate extraneous magnetic field interference, for example from the earth's magnetic field or surrounding electronic equipment. For fields below the strengths of approximately 500 Gauss of magnetic field 470 along the NV axis, a simple linear model can reliably approximate steady state solutions of the spin resonance. At strengths above 500 Gauss, unrelated effects of nuclear spin polarization can occur. Accordingly, in an exemplary embodiment, the magnetic field 470 can be approximately 100 Gauss.

For purposes of illustration and not limitation, the number of resolvable NV centers can roughly correlate to the magnetic moment projected onto the incident magnetic field divided by the average linewidth of an electron spin resonance line. This correlation is analogous to that used in connection with magnetic resonance imaging (MRI). For example, and not limitation, if a magnetic field 470 of 100 G is applied with a magnetic moment of 2.5 MHz/G and an ESR linewidth of 5 MHz, approximately 50 NV centers can be resolved.

As noted above, by exposing the NV centers to a magnetic field 470, the degeneracy of the "dark" $m_s=\pm 1$ states is lifted via the Zeeman effect. The energy difference between the two dark states can be given by, e.g., $\mu B \cos(\theta)$, where $\theta$ is the angle of the applied magnetic field, B, 470, with respect to the axis of each NV center and $\mu$ is the electron magnetic moment. Thus, the field splitting frequency for the $m_s=\pm 1$ states can differ from the zero field splitting frequency (i.e., approximately 2.87 GHz notwithstanding certain other factors) and can differ from each other by an amount corresponding to the energy difference between them.

The nitrogen vacancy centers of the sample 420 can be optically excited (330) with, for example, a light source 410. In one embodiment, for example, the light source 410 can optically excite the nitrogen vacancy centers with a continuous wave of pump light at approximately 523 nm 411. In certain embodiments, as described in more detail below, the light source 410 can be configured (e.g., through coupling to a control unit 490) to generate pump light in a pulsed fashion to first optically excite the nitrogen vacancy centers, and then generate a readout pump light after, e.g., a sequence of microwave pulses such as a Rabi sequence or other echo sequence.

In certain embodiments, wide-field, speckle-free illumination with 530 nm polarized light upon a sample containing NV centers can be employed 416. For example, a broad field green illumination laser can be used. Certain optics 450, such as an objective lens and/or one or more apertures, can also be included to have a broad field light 412 on the focal plane. The broad field green illumination laser 416 can be operated at, for example, an incident power of approximately 2.8 kW/cm$^2$. Alternatively, a focused field laser 415 can be used. The focused field laser 415 can be operated at a power of approximately 1.25 kW/cm$^2$. In certain embodiments (e.g., in connection with the use of certain reconstruction algorithms similar to those used in STORM and PALM), light source 410 can include two lasers for charge state control. For example, a pump laser above 579 nm wavelength and a reset laser approximately equal to 450 nm can be used.

In certain embodiments, light from the light source 410 can be reflected or otherwise manipulated with one or more dichroic and/or flip mirrors and/or filters (441, 446, 440, 445), which can be reflective over certain wavelength ranges and transparent over others. For example, a mirror 441 can be used to reflect focused field light 411 from the focused field laser 415. In like manner, mirror 446 can be used to reflect broad field light 412 from broad field laser 416. A dichroic mirror 440 can reflect the incident light (e.g., 411 or 412) to the sample 420, e.g., in connection with conventional microscopy optics 455. That is, dichroic mirror 440 can be reflective over a wavelength range of the incident light. Additionally, Dichroic mirror 440 can, for example, be transparent over a wavelength range corresponding to a fluorescent response 413 of the NV centers, which can be, for example, between approximately 637 nm and approximately 800 nm.

As noted above, optically exciting the NV centers can drive the NV centers into an excited $^3$E state, which can then relax back down to the $^3$A ground state (i.e., the NV centers can absorb photons with a wavelength around 532 nm and emit a fluorescent response, which can be between 637 and 800 nm). The transition between the ground state to the excited state can be spin conserving. However, the relaxation pathway through spin-dependent intersystem crossing ($^1$A) between excited state ($^3$E) triplet to a metastable, dark singlet level ($^3$A) can change the integrated fluorescent response for the spin states |0⟩ and |±1⟩. Because deshelving from the singlet occurs primarily to the |0⟩ spin state, continuous optical pumping can provide a means to polarize the NVC to the |0⟩ spin state. Moreover, relaxation through the spin-dependent intersystem crossing does not emit a photon in the visible spectrum. Thus, the fluorescent response of the system can correspond to populations of |0⟩0 and |±1⟩ spin states, where an increase in the $m_s=\pm 1$ populations correspond to a lower intensity fluorescent response.

Accordingly, the nitrogen vacancy centers can be "switched" from a dark state to a bright state or from a bright state to a dark state by applying at least one microwave pulse (340). Applying a microwave pulse equal to the field splitting frequency of a nitrogen vacancy center can drive the spin state from the $m_s=0$ state to the $m_s=\pm 1$ state. For example, assuming degeneracy of the $m_s=\pm 1$ states (i.e., without application of a magnetic field or certain other factors), the field splitting frequency can be equal to approximately 2.87 GHz. Thus, applying approximately a 2.87 GHz microwave pulse to the nitrogen vacancy centers can increase the population of spin states toward the $m_s=\pm 1$. As noted above, in the presence of magnetic field 470, the degeneracy of the $m_s=\pm 1$ states is broken such that the $m_s=-1$ state corresponds to a certain field splitting frequency and the $m_s=\pm 1$ state corresponds to another field splitting frequency (the frequency depending on the orientation of the NV axis with respect to the magnetic field 470. That is, the electron spin resonance (ESR) spectrum includes two dips (i.e., dark "spots") corresponding to the $m_s=+1$ and the $m_s=-1$ spin states, as illustrated in FIG. 1 as spectrum 190. Because the field splitting frequency corresponds to the orientation of the NV axis with respect to the magnetic field 470, individual NV centers can be uniquely addressed. For example, for a plurality of diamond nanocrystals, there can be a large number of unique orientations of NV centers with respect to the magnetic field 470, and thus individual NV centers can have a high probability of having a unique orientation, and thus a unique field splitting frequency.

The microwave pulse can be applied, for example, using a microwave emitter 460 such as a strip line or other suitable homogenously emitting antenna. The microwave emitter 460 can be coupled to a control unit 490 (connection not shown) or other suitable control instrumentation. The microwave emission can be tuned, e.g., using the control unit 490 to a predetermined frequency, such as corresponding to a field splitting frequency of the NV center.

In one embodiment, a microwave pulse can be tuned to a field splitting frequency of one of the nitrogen vacancy centers in the sample 420 (e.g., either to the $m_s=+1$ or the $m_s=-1$ state). This microwave pulse can increase the population of the $m_s=\pm 1$ states, and thus modulate the intensity of the fluorescent response 413. Additionally, other microwave pulses can be tuned to a field splitting frequency of other NV centers in the sample 420. In certain embodiments, a plurality of microwave pulses can be applied to obtain a substantially full ESR spectrum of one or more NV centers.

The fluorescent response 213 of the nitrogen vacancy centers can be detected (350), and the fluorescent response 213 can be processed (360) to resolve at least one NV center. As disclosed herein, certain embodiments can enable the resolution of NV centers within a diffraction-limited spot (e.g., down to approximately 30 nm). Detection of the fluorescent response can be accomplished, e.g., with an array of pixels 430, such as a CCD or emCCD array. In certain embodiments, the array of pixels 430 can include a 13×13 array over an area of 1 micron. Suitable magnification onto a CCD array (which can be, e.g., 512×512 or 1024×1024 pixels) can depend on the background noise and the expected number of photons for a given integration time. For a bright emitter such as the NV and using high-end CCDs, a magnification of approximately 16 µm/85 and approximately 200× can be used. That is, for example, each pixel on the CCD can correspond to about 80 nm of the sample. Higher magnification can enhance measurements for higher-end array detectors with lower readout noise and dark counts, in accordance with equation 2, below. In certain embodiments, a confocal scanning technique can be employed. In certain embodiments, a wide field of view can be captured. The control unit 490 can process the fluorescent response from the array of pixels 430 and generate a full ESR spectrum for each pixel. By one or more processors and/or other circuits in control unit 490, spectrum can be fit with a sum of Lorentzian dips, and contrasts from the fits can be used as an intensity map for uniquely addressable NVs. In certain embodiments, the control unit 490 can also include one or more memories coupled to the one or more processors and/or other circuits including computer code, which when executed can cause the one or more processors to perform desired functions.

By comparing an image of an NV being resonantly driven with an image of an NV being off-resonantly driven, only the lowered fluorescence from the resonantly excited center is seen in the subtraction of the two images as shown in FIG. 1c. The signal to noise ratio of this subtracted image can be approximately given by $$\frac{N}{\sigma} \propto \frac{\gamma\tau\eta C}{\sqrt{\gamma\tau\eta(M-1)+\gamma\tau\eta(1-C)}}, \quad (1)$$

where $\gamma$ is the fluorescence rate, $\tau$ is the acquisition time, $\eta$ is the collection efficiency, C is the fractional decrease of the total fluorescence on resonance, and M is the total number of emitters in a collection volume. For imaging with a two-dimensional CCD array, substitution of equation 1 into an analytical solution can provide a shot-noise-limited $$\langle(\Delta x)^2\rangle \approx \frac{s^2}{N}\left(1+\frac{1}{12}\left(\frac{a}{s}\right)^2+\frac{8\pi}{\left(\frac{a}{s}\right)^2}\frac{M-C}{C}\right) \quad (2)$$

where s is the standard deviation of the Gaussian distribution, N is the total number of signal photons collected, and a is the pixel size divided by the magnification. Assuming no resonance lines and after an acquisition time of approximately 5 s, an NV center can be distinguished from a cluster of approximately 100 centers with a resolution $\Delta x$ of approximately 30 nm.

For purposes of illustration and not limitation, certain non-limiting examples of the disclosed subject matter will now be described in detail.

Figure 5:
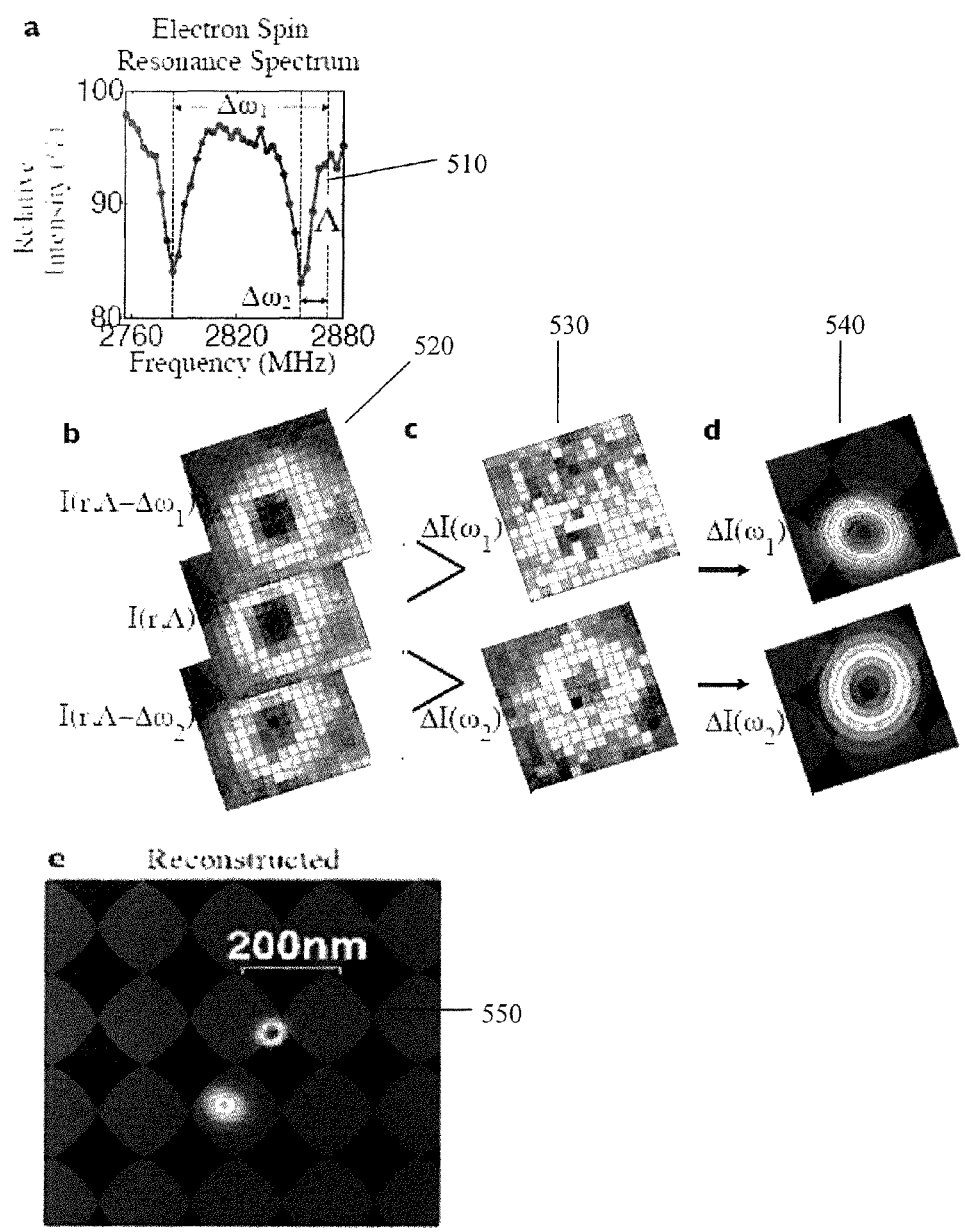
FIG. 5 is an illustrative demonstration of resolving two NV centers within a diffraction-limited focal spot in accordance with an embodiment of the disclosed subject matter.

In one exemplary embodiment, a scanning confocal technique can be employed. For example, and not limitation, a confocal scan can include a 13 by 13 pixilated image over a square area of approximately 800 nm×800 nm including two NV centers. With reference to FIG. 5, an exemplary ESR spectrum 510 can be generated. For each pixel, the microwave field can be scanned over three separate frequencies; the first resonant with one NV– center, the second being off resonant from both centers, and the third being resonant with the second NV center. One of ordinary skill in the art will appreciate that the order of frequencies can be varied. With the three intensity plots 520, each at different frequencies, the differences 530 between the intensity plots for each center can be generated. Using, e.g., a least squares method fitting routine 540, each NV center can be resolved 550. As illustrated in FIG. 5, the NV centers were resolved 195 nm apart with a resolution of 35 nm. In certain embodiments, the number of frequency steps per pixel can correspond to the number of NV centers contained within the scanning area. Additionally, in certain embodiments, a full ESR spectrum can be generated for each pixel.

For purposes of illustration, and not limitation, a two-dimensional confocal scan with a total of m NV centers can be given by:

$$I(x,y,\omega)=\Sigma_i^m I_i \alpha_i [1-D_i(P_{RF},P_{pump},\omega)N_i(x,y)], \quad (3)$$

where I is intensity, $\alpha$ is collection efficiency; $D_i$ is electron spin resonance dips; $P_{RF}$ is power of the radio-frequency field; $P_{pump}$ is the power of the optical 532 nm pump field;

$\omega$ is the crystal field splitting frequency, and N is a two-dimensional Gaussian distribution with general defining parameters. In certain embodiments, a symmetric Gaussian (that is, with $\sigma_x=\sigma_y$) can also be used for fitting the subtracted data. A confocal scan taken off resonance can be subtracted from a confocal scan taken on resonance to isolate only the photons emitted from the NVs with frequencies $\omega_i$, given by:

$$I(x,y,\omega_0)-I(x,y,\omega_i)=I_i\alpha_iC_i(P_{RF},P_{pump})N_i(x,y) \quad (4)$$

$D_i$ can be given by:

$$Di(P_{RF}, P_{pump}, \omega) = \frac{C_i(\gamma_i/2)^2}{(\gamma_i/2)^2 + (\omega - \omega_i)^2}, \quad (5)$$

where $C_i(P_{RF}, P_{pump})$, $\gamma_i(P_{RF}, P_{pump})$, and $\omega_i=\omega_0\pm\vec{B}\cdot\vec{\mu}_i$. $N_i(x,y)$ can be given by:

$$N_i(x, y) = \frac{e^{\frac{-1}{2(1-\rho_i^2)}\left[\frac{(x-\mu_{ix})^2}{\sigma_{ix}^2} + \frac{(x-\mu_{iy})^2}{\sigma_{iy}^2} - \frac{2\rho_i(x-\mu_{ix})(x-\mu_{iy})}{\sigma_{ix}\sigma_{iy}}\right]}}{2\pi\sigma_{ix}\sigma_{iy}\sqrt{1-\rho_i^2}}. \quad (6)$$

A confocal scan can be performed and/or an emCCD array can be used to detect fluorescent responses of the nitrogen vacancy centers. In one embodiment, for example, for each pixel in the array, a microwave field applied can dwell upon three separate frequencies: $\omega_{-1}$, $\omega_0$, and $w_{\omega+1}$. Three intensity plots can be recorded, each corresponding to one of the three separate frequencies. That is, for each frequency, the array of pixels can record an intensity measurement at each pixel. By doing the subtraction $I(x, y, \omega_0)-I(x, y, \omega_{\pm 1})$, the same NV center can be isolated twice. In certain embodiments, the dwell time for each microwave emission can be approximately 200 ms.

In another exemplary embodiment, a wide-field imaging technique can be employed, in which an entire image, $I(r,w)$, can be acquired simultaneously using a two-dimensional detector array. In this embodiment, total acquisition time can be significantly reduced relative to the confocal scanning technique described above.

For purposes of example, and not limitation, an emCCD array with a magnification of approximately 200× and a laser with power of approximately 1.25 kW/cm² can be used over a 60 um diameter field. The emCCD and magnification optics can be arranged such that each pixel of the emCCD array can correspond to 85 nm of a sample. As such, each diffraction-limited spot can be fully encapsulated in an image of approximately 7×7 pixels. Each capture can have an exposure time of, for example, 450 ms. Microwave emission can step between 2.65 GHz to 2.9 GHz, and the number of steps can be, for example, approximately 51. For example, the emCCD can capture one frame for each of 51 steps in a microwave frequency sweep. In certain embodiments, this can be repeated and averaged, e.g., approximately 10 times.

Figure 6:
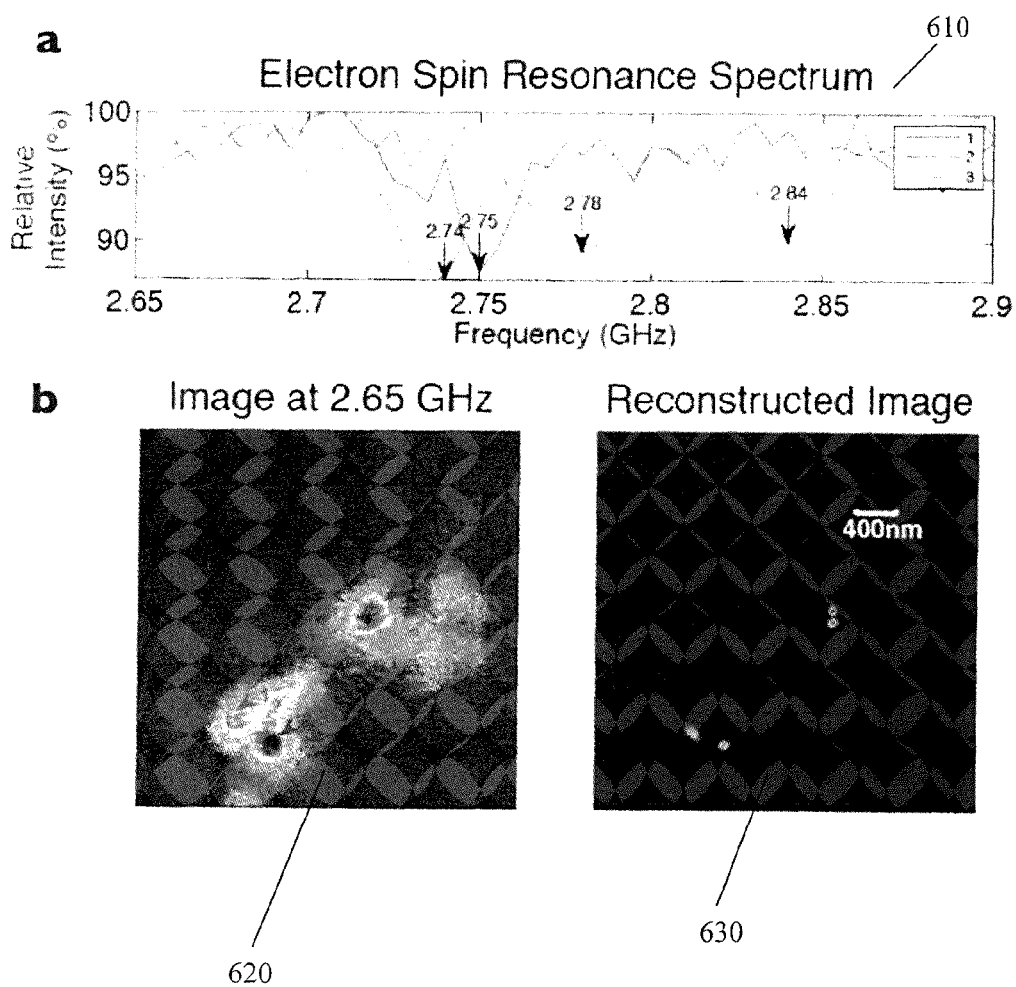
FIG. 6 is an illustrative demonstration of resolving NV centers within wide field of view in accordance with an embodiment of the disclosed subject matter.

With reference to FIG. 6, the intensity of each NV can be plotted as a function of microwave frequency applied, depicting the ESR spectrum 610 across a large field of view. An image 620 can be generated over a wide field of view illustrated resolvable NV center areas. Moreover, within each resolved area, individual NVs can be resolved using a few frequency points that are resonant with the areas of interest, as illustrated in reconstructed graph 630.

In certain embodiments of the disclosed subject matter, pulsed measurements can be used over a wide field of view. For example, in connection with, e.g., an intensified CCD (iCCD), dynamic decoupling techniques such as Rabi, Ramsey and/or Echo measurements of many NV centers can be utilized during confocal excitation and collection. In connection with such embodiments, such measurements can also be performed in parallel over a wide field of view using an iCCD or, in general, any array of detectors sensitive enough to detect single photons.

In another exemplary embodiment, the techniques disclosed herein above can be used in connection with Forster resonance energy transfer (FRET) techniques to obtain nm-scale resolution. For example, a fluorophore with an absorption spectrum at least partially overlapping with the emission spectrum of the NV centers can be provided to a sample. The fluorescent response of the NV center can non-radiatively excite the fluorophore if the NV is within a certain distance of the fluorophore. The fluorescent response of the fluorophore can be detected, and proximity information between the NV and the fluorophore can be resolved. Such an energy transfer from the NV to the fluorophore can occur by a dipole-dipole coupling effect. For the FRET phenomenon described herein, transfer of more than 50% of the energy can occur, for example, when the distance between the two molecules fall within a Forster distance, which can be approximately 10 nm in length. Accordingly, the techniques disclosed herein can provide for resolution of the proximity of a NV and a fluorophore to on the order of tens of nanometers or less.

Additionally or alternatively, in connection with FRET techniques, the techniques disclosed herein can enable the determination of an orientation of a magnetic dipole of a molecule coupled to a fluorophore. Due to the strong magnetic moment of the electron, any nearby magnetic fields can induce a Zeeman splitting of the $m_s=+1$ and the $m_s=-1$ ground state levels. Such a Zeeman effect can be optically detected. Alternatively, sensitive measurement of magnetic fields with the NV centers can include a pulsed scheme such as spin-echo or dynamic decoupling techniques as disclosed herein.

Moreover, the techniques disclosed herein can further enable the probing of a local environment. For example, the presence of a local magnetic field, electric field, or inhomogeneous pH can alter the fluorescent response of the NV centers. Accordingly, changes in these environmental characteristics can be determined by observing differences in the fluorescent response of the NVs. Changes in the electron spin orientation or the charge state of the NV– can be measured by the fluorescence brightness and spectrum.

As described above in connection with certain embodiments, a control unit 490 is provided to process the fluorescent response from the array of pixels 430 and generate a full ESR spectrum for each pixel and fit the spectrum with a sum of Lorentzian dips, such that contrasts from the fits can be used as an intensity map for uniquely addressable NVs. In these embodiments, the control unit 490 plays a significant role in enabling the resolution of nitrogen vacancy centers, e.g., below the diffraction limit. For example, the presence of the control unit 490 provides the ability to provide near real-time feedback to, e.g., the tunable microwave emitter, the light source, and provides the ability to isolate unique NV centers. Such techniques could not be performed merely in the mind or with pen and paper.

Certain techniques for fluorescence microscopy can enable spatial resolution below the diffraction limit by localizing multiple temporally or spectrally distinguishable fluorophores. For purpose of illustration and not limitation, techniques in accordance with some embodiments of the disclosed subject matter can provide super-resolution microscopy by deterministically controlling the brightness of uniquely addressable, photo-stable emitters. The fluorescence brightness of negatively charged NV centers in nanodiamonds can be modulated through magnetic resonance techniques. Such deterministic emitter switch microscopy (DESM) techniques can enables super-resolution imaging with localization down to 12 nm across a 35×35 µm$^2$ area. DESM can be well suited for biological applications such as multi-spectral particle tracking at least in part because fluorescent nanodiamonds can be cytocompatible, non-bleaching, and bright. Additionally or alternatively, fluorescence count rates exceeding 1.5×10$^6$ photons per second can be observed from single NV centers at saturation. Additionally or alternatively, DESM can be combined with emerging NV-based techniques for sensing magnetic and electric fields, for example, to allow rapid, super-resolution imaging for tracking and sensing applications in the life and physical sciences.

In sub-diffraction limited microscopy, it can be challenging to localize multiple fluorescent emitters within a diffraction volume. To locate and discriminate several emitters, their fluorescence can be distinguished or resolved sufficiently to reconstruct individual spatial locations. An NV center can be appealing for fluorescence microscopy due to its photostability and brightness. These properties can enable certain techniques such as stimulated emission depletion (STED) microscopy to resolve NV centers down to 5.8 nm by scanning a high power (~1 GW/cm$^2$) doughnut-shaped depletion spot across a sample. However, such serial scanning measurement can result in a slow frame rate—approximately 25 seconds for a 0.3×0.3 µm$^2$ field of view—which can preclude imaging of important dynamical process, especially in biological sciences. NV spin manipulation techniques can allow for a reduced laser excitation intensity, but can involve a reduced acquisition speed. Certain stochastic super-resolution techniques, such as photo-activated localization microscopy (PALM) and stochastic optical reconstruction microscopy (STORM), can employ sequential activation of photo-switchable fluorophores for time-resolved localization. Such methods can enable fast, parallel acquisition using two-dimensional (2D) charge-coupled device (CCD) arrays. For example, STORM can reach a frame acquisition time of 30 seconds for 20 nm spatial resolution over a 13×4 µm$^2$ field of view using a bleaching laser power of approximately 15 kW/cm$^2$. However, stochastic super-resolution techniques can involve precise control of the maximum density of fluorophores, localization of stochastic switching events over diffuse background, and trade-offs between photostability and imaging rate.

DESM can employs deterministic modulation of emitters with spin-dependent fluorescence that can be uniquely addressable, photostable, and bright, for example, with more than 1.5×10$^6$ photons observed per emitter per second. Through selective microwave excitation of the spin-triplet ground state, it can be possible to control the fluorescence rates of tens to hundreds of uniquely addressable classes of NV centers in nanodiamonds, as described herein. This multi-spectral probing in the microwave domain can allow multi-color particle tracking and imaging. Certain techniques for ESR addressability for sub-diffraction microscopy of NV centers can be applied over a ~25×20 nm$^2$ field of view. DESM can achieve a resolution of 12 nm over a 35×35 µm$^2$ field of view and can have an integration time of ~90 seconds using continuous excitation with a laser intensity of approximately 30 kW/cm$^2$. DESM techniques can enable high-speed, sub-diffraction limited imaging with low laser intensity across a wide field of view.

Figure 7:
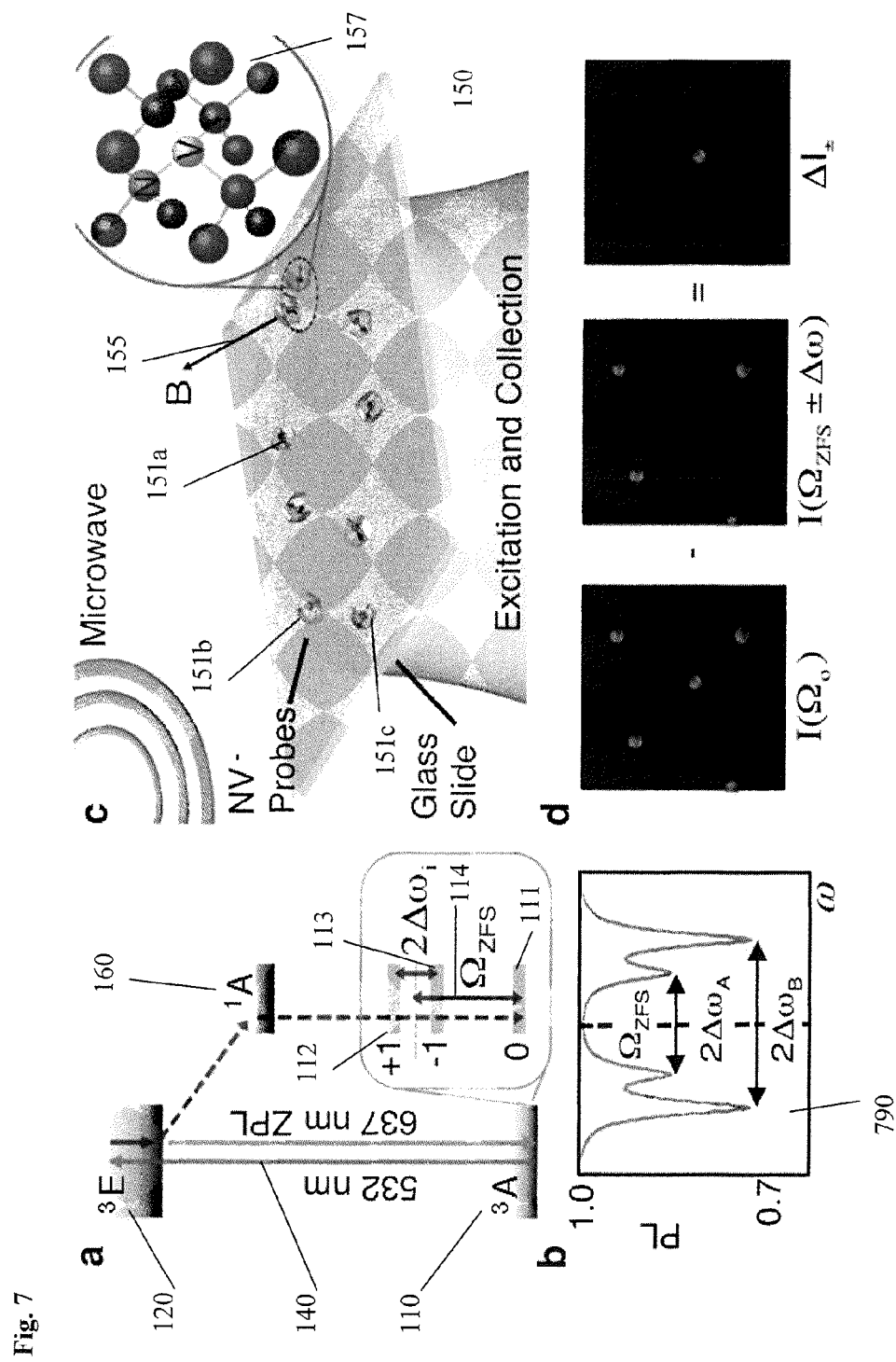
FIG. 7a is a diagram showing an exemplary NV center in diamond in accordance with an embodiment of the disclosed subject matter.
FIG. 7b illustrates the fluorescence spectrum of two NV centers in the presence of a static magnetic field as a function of applied microwave frequency in accordance with an embodiment of the disclosed subject matter.
FIG. 7c illustrates an exemplary sample including a plurality of NV centers in accordance with an embodiment of the disclosed subject matter.
FIG. 7d illustrates an exemplary technique of resolving an NV center in accordance with an embodiment of the disclosed subject matter.

FIG. 7a is a diagram showing an exemplary NV center in diamond in accordance with an embodiment of the disclosed subject matter. The exemplary NV center depicted in FIG. 7a can be similar to the NV center depicted in FIG. 1a. For purpose of illustration and not limitation, the NV energy level diagram depicted in FIG. 7a can show how preferential shelving of the $|m_s=\pm 1\rangle$ (112 and 113) sub-levels from the excited state ($^3$E) 120 into the dark metastable state ($^1$A) 110 can give rise to a typical ESR spectrum. The fluorescence intensity of the NV can depend on occupation of the three sub-levels of its spin triplet. In the $|m_s=0\rangle$ 111 "bright" sub-level, the center can be photostable and bright; in the $|m_s=\pm 1\rangle$ 112 and 113) "dark" sub-levels, the center can undergo intersystem crossing into a metastable spin-singlet state that can reduce the average fluorescence intensity. The energy of the $|m_s=\pm 1\rangle$ (112 and 113) ground states can exceed the $|m_s=0\rangle$ 111 state by the crystal field splitting, $\Omega_{ZFS} \approx 2.87$ GHz, in the absence of external magnetic fields. The degeneracy of the ±1 (112 and 113) states can be lifted in the presence of a weak magnetic field via the Zeeman effect. In this regime, the energy difference between the two dark states can be given by $2\Delta\omega \approx 2g\vec{\mu}\cdot\vec{B}$, where g is the electronic Landé g-factor, $\vec{\mu}$ is the NV$^-$ magnetic moment, and $\vec{B}$ is the applied magnetic field. Continuous optical polarization of the NV into $|m_s=0\rangle$ 111 using concurrent microwave excitation can decrease the NV fluorescence when the microwave field is resonant with the $|m_s=\pm 1\rangle$ (112 and 113) transitions.

FIG. 7b illustrates the fluorescence spectrum 790 of two NV centers in the presence of a static magnetic field as a function of applied microwave frequency in accordance with an embodiment of the disclosed subject matter. For purpose of illustration and not limitation, the fluorescence of two NV$^-$ centers in the presence of a static magnetic field can be modeled as a function of applied microwave frequency. The splitting of the two dips ($2\Delta\omega_{A,B}$) can be given by the projection of the incident magnetic field on the magnetic moment of the NV ($2g\vec{\mu}_{A,B}\cdot\vec{B}$). For example, the contrast of each dip can have an inverted Lorentzian shape, and a minimum line width can be limited by the dephasing time due to the environment ($T_2^*$). Such an ODMR technique can enable measurement of the electron spin resonance frequencies of all centers within the optically excited region on a sample. For example, the NV centers within a diffraction-limited spot can have non-overlapping resonances or partially overlapping resonances, and the NV centers can be individually addressed by microwave excitation and deterministically driven into the dark state.

FIG. 7c illustrates an exemplary sample including a plurality of NV centers in accordance with an embodiment of the disclosed subject matter. The sample depicted in FIG. 7c can be similar to the sample depicted in FIG. 1b. For purpose of illustration and not limitation, referring to FIG. 7c, NV centers (151a, 151b, 151c) in a static magnetic field each can have field splitting frequencies corresponding to their uniquely oriented magnetic moments relative to the magnetic field 155. To measure ESR spectrums across a wide field of view, the average fluorescence intensity can be measured across hundreds of diffraction limited sites (dotted circle) while the frequencies of microwave pulses are swept or scanned through a range.

FIG. 7d illustrates an exemplary technique of resolving an NV center in accordance with an embodiment of the disclosed subject matter. The technique illustrated in FIG. 7d can be similar to the technique depicted in FIG. 1c. For purpose of illustration and not limitation, referring to FIG. 7d, the difference between two images can be taken where a uniquely addressed emitter is and is not dimmed by resonant microwave excitation, $I(\Omega_{ZFS} \pm \Delta\omega)$ and $I(\Omega_0)$, respectively. By subtracting the image where the emitter is dimmed, $I(\Omega_{ZFS} \pm \Delta\omega)$, from the image where the emitter is not dimmed, $I(\Omega_0)$, the location of the emitter can be shown in the resulting image, $\Delta I_{\pm}$.

For purpose of illustration and not limitation, nanodiamonds can be arbitrarily oriented on a surface, which can lead to a wide range of non-degenerate spin transitions uniquely associated with individually oriented NV centers. The number of uniquely addressable centers can depend at least in part on the number of non-overlapping or partially overlapping Lorentzian resonances over the peak frequency splitting due to an applied magnetic field. For example, each NV center can have a splitting of approximately 2.8 MHz/G for the magnetic field magnitude parallel to the NV axis. In some exemplary embodiments, for an applied field of 200 Gauss, up to an estimated ~55 uniquely addressable classes of NV centers can be resolved within a diffraction limited spot. With stronger applied fields along the perpendicular plane to the NV axis, the ESR spectrum contrast can decrease due to electron spin mixing of the sub-levels.

In some embodiments, sub-optical resolution can be achieved by multi-spectral imaging in the microwave domain. For example, each of the NV centers within a diffraction limited spot can be individually dimmed by resonantly driving only one ground-state spin transition at a time. As shown in FIG. 7d, the fluorescence from a single addressed NV center remains in the subtracted image $\Delta I_{\pm}$ after subtracting an image acquired with resonant microwave excitation from an image obtained without resonant excitation. For purpose of illustration and not limitation, the signal-to-noise ratio of this subtracted image can be approximated by:

$$\frac{N}{\sigma} \sim \frac{\eta \tau \Gamma(I_{laser}) C}{\sqrt{\eta \tau \Gamma(I_{laser})(M-1) + \eta \tau \Gamma(I_{laser})(1-C) + A I_{laser} + B}} \quad (7)$$

where N is the number of collected signal photons, σ is the noise, η is the collection efficiency, τ is the acquisition time, $\Gamma(I_{laser})$ is the fluorescence rate as a function of laser intensity $I_{laser}$, C is the fractional decrease of the total fluorescence on resonance, and M is the total number of emitters in the collection volume. A accounts for linearly increasing background with laser intensity, and B can be a constant background noise. As seen in this equation, for other kinds of emitters with a larger switching contrast, C, a greater number of emitters can be resolved per site, as discussed below. For purpose of illustration and not limitation, when imaging with an exemplary 2D CCD array, a shot-noise-limited measurement error for estimating the center of a two-dimensional Gaussian spot can be given by:

$$\langle (\Delta x)^2 \rangle = \frac{s^2}{N} \left[ 1 + \frac{1}{12} \left( \frac{a}{s} \right)^2 + \frac{8\pi}{\left( \frac{a}{s} \right)^2} \frac{M-C}{C} \right] + \theta(N^{-2}) \quad (8)$$

where s is the standard deviation of a point spread Gaussian distribution, and a is the camera pixel size divided by the magnification. The derivation of this equation is discussed below. In some embodiments, this analytical result can underestimate the actual error by up to ~30%.

Figure 8:
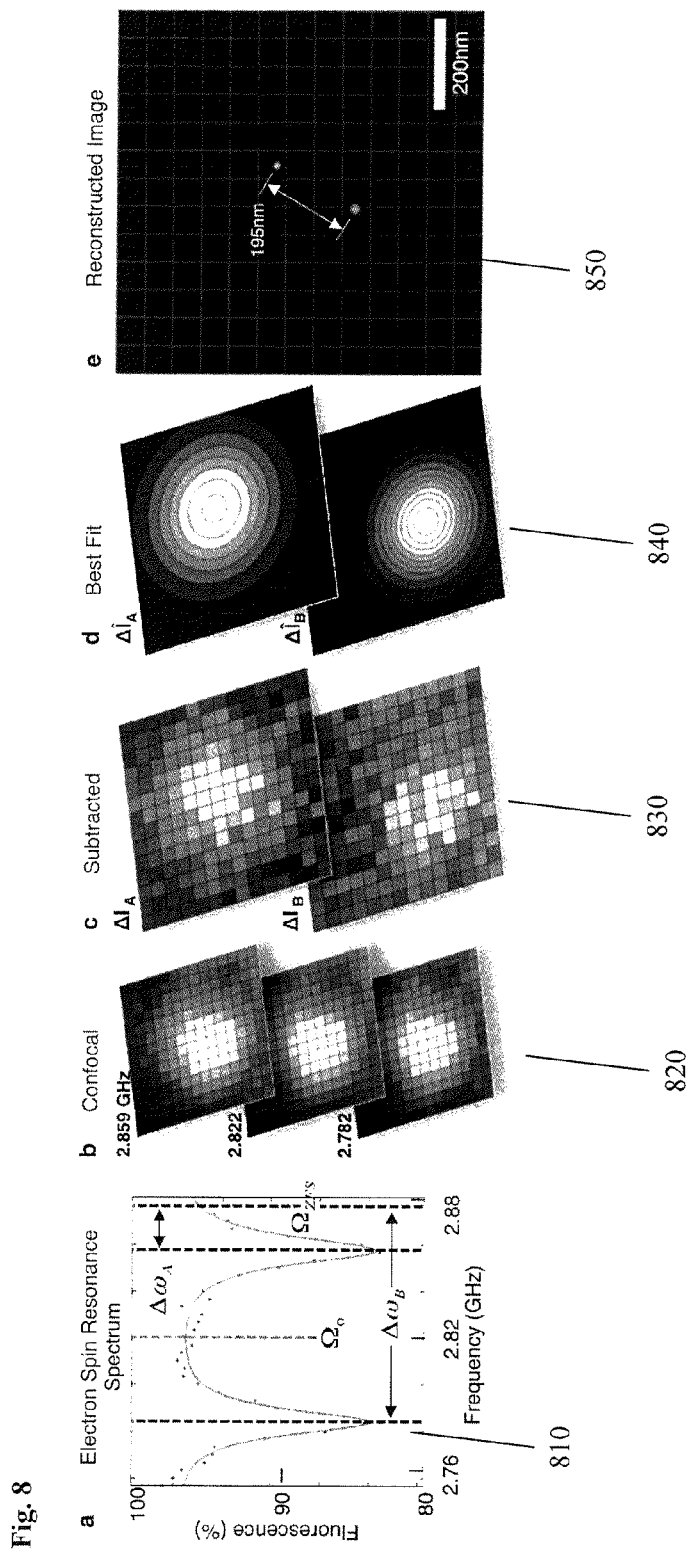
FIG. 8 is an illustrative demonstration of resolving two NV centers within a diffraction-limited focal spot in accordance with an embodiment of the disclosed subject matter.

FIG. 8 is an illustrative demonstration of resolving two NV centers within a diffraction-limited focal spot in accordance with an embodiment of the disclosed subject matter. For purpose of illustration and not limitation, FIG. 8a can show an ESR spectrum 810 of two NV centers of different orientations in a diffraction limited site under a static magnetic field. The curve can be an inverted Lorentzian fit to the data. An exemplary ESR spectrum 810 can be generated. For each pixel, the microwave field can be scanned over three separate frequencies; the first resonant with one NV center, the second being off resonant from both centers, and the third being resonant with the second NV center. One of ordinary skill in the art will appreciate that the order of frequencies can be varied. FIG. 8b can depict three 14×14 intensity plots 820 from confocal scans over a 0.8×0.8 μm² area, with each scan taken at three different applied microwave excitation frequencies: $\Omega_{ZFS}-\Delta\omega_A$, $\Omega_o$, $\Omega_{ZFS}-\Delta\omega_B$. With the three intensity plots 820, each at different frequencies, the differences 830 between the intensity plots for each center can be generated. FIG. 8c can depict subtraction 830 of images where emitters are resonantly and not resonantly excited. Using, e.g., a symmetric Gaussian least squares method fitting routine 840, each NV center can be resolved 850. For example, FIG. 8d depicts symmetric Gaussian fits 840 to the subtracted images 830, and FIG. 8e depicts a reconstruction 850 of the two NV centers within a diffraction-limited spot in accordance with the subtraction 830 and fitting 840. The full-width half-maximum of the top and bottom Gaussians can be 11 nm and 16 nm, respectively. As illustrated in FIG. 8, the NV centers can be resolved 195 nm apart with resolutions of 11 nm and 16 nm for the top and bottom Gaussians, respectively. In certain embodiments, the number of frequency steps per pixel can correspond to the number of NV centers contained within the scanning area. Additionally, in certain embodiments, a full ESR spectrum can be generated for each pixel.

For purpose of illustration, various imaging modalities can be used, including but not limited to confocal imaging, which can allow for enhanced optical resolution and contrast, and wide-field imaging, which can enable sub-diffraction limited imaging of hundreds of NV centers simultaneously. For example, for an NV site on a bulk diamond sample, an ESR spectrum 810 of two emitters, A and B, can be obtained, and the number of emitters can be verified by autocorrelation measurements, as discussed below. The spectrum obtained at the position of peak intensity can show that emitters A and B can have different splittings of $\Delta\omega_A$=13 MHz and $\Delta\omega_B$=87 MHz, respectively, which can indicate different NV orientations. For purpose of illustration and not limitation, confocal imaging can be performed using a home-built confocal microscope with a Nikon 100× objective (NA=1.3), an avalanche photon detector (APD), and a 532 nm pump laser at a power of 1,500 μW. For example, for super-resolution confocal imaging, the $|m_s=-1\rangle$ ground state resonances can be used and the fluorescence intensity plots 820 at three microwave frequencies can be acquired, with two frequencies each being resonant with a corresponding one of the two centers and a third frequency being off-resonant from both NV centers: $\Omega_{ZFS}-\Delta\omega_A$, $\Omega_0$, and $\Omega_{ZFS}-\Delta\omega_B$. Fitting the difference plots 830, $\Delta I_{A,E}(\vec{r})=I(\vec{r},\Omega_O)-I(\vec{r},\Omega_{ZFS}-\Delta\omega_{A,B})$ with symmetric Gaussian functions by a least-squares method 840 can produce the reconstructed image 850, which can indicate emitter localization with resolution down to 11 nm with an ~80% coefficient of determination and a separation of 195 nm. Additionally, each additional emitter 'k' with $|m_s=0\rangle \rightarrow |m_s=\pm 1\rangle$ transition frequencies $\Omega_{ZFS}\pm\Delta\omega_k$ can be localized by acquiring additional images, $I(\vec{r},\Omega_{ZFS}\pm\Delta\omega_k)$, and the same image subtraction and Gaussian fitting can be used.

Figure 9:
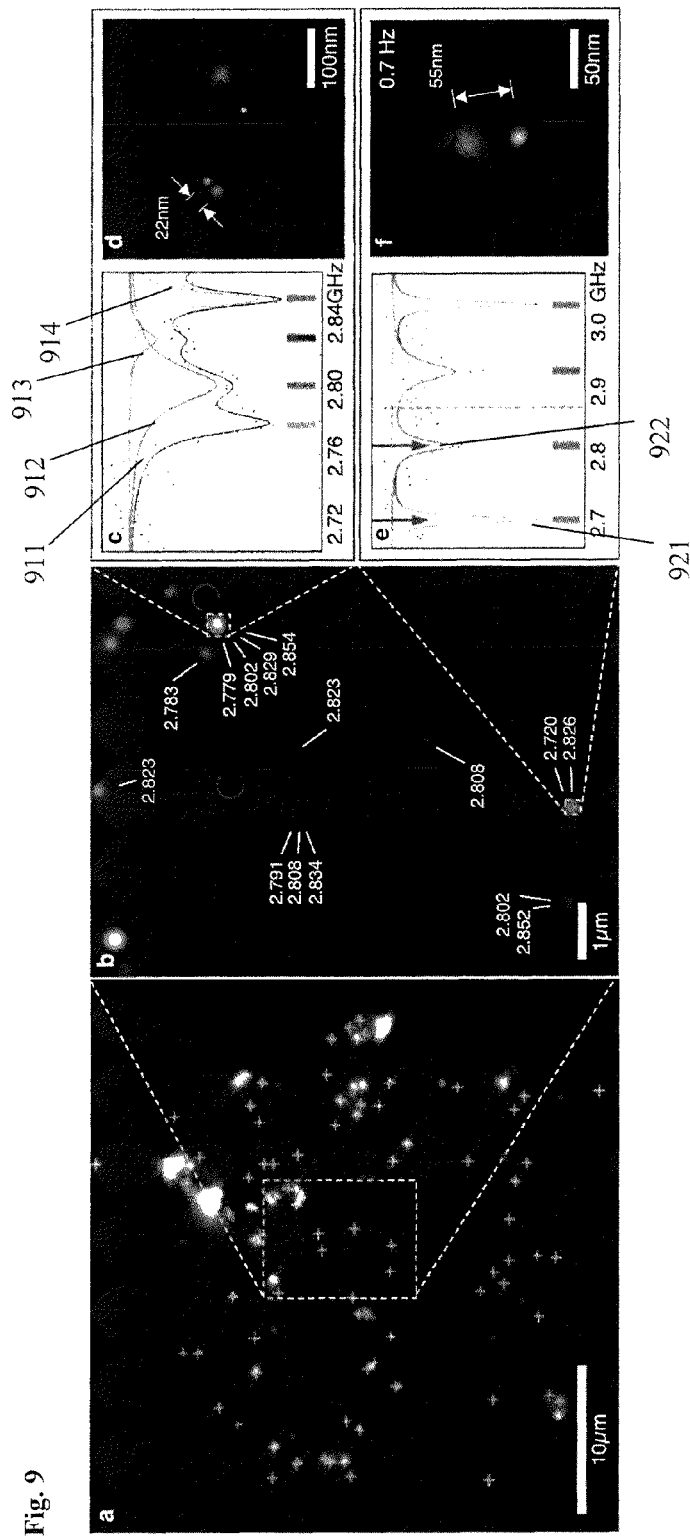
FIG. 9 is an illustrative demonstration of resolving NV centers within wide field of view in accordance with an embodiment of the disclosed subject matter.

FIG. 9 is an illustrative demonstration of resolving NV centers within wide field of view in accordance with an embodiment of the disclosed subject matter. FIG. 9a depicts an exemplary fluorescence image of nanodiamonds over a 35×35 µm² area. The '+' markings can indicate sites that show ESR modulation, and the 'x' markings can indicate sites that do not show modulation. FIG. 9b depicts an exemplary reconstructed image of a region from FIG. 9a (shown by the dotted line) after resolving the NV centers therein, and the circles can indicate a lack of ESR modulation. Using an ESR spectrum at each site, multi-emitter sites can be reconstructed, for example, over a 7×9 µm² field of view. The numbers superimposed on the image can correspond to the resonance frequencies of each NV in the site. FIG. 9c depicts an exemplary ESR spectrum of a multi-spectral site from FIG. 9b. The Lorentzian fits (911, 912, 913, 914) can correspond to the resonances of each of four exemplary NV centers in the site. FIG. 9d depicts an exemplary sub-diffraction limited reconstruction of the four exemplary NV centers in FIGS. 9b and 9c. Full-width half-maximum for each NV center from left to right can be: 26 nm, 15 nm, 12 nm, 46 nm, respectively. FIG. 9e depicts an exemplary full ESR spectrum of a site containing two exemplary NV centers. Lines 921 and 922 can indicate Lorentzian fits for each center, and the arrows can indicate the resonance frequencies at which images were taken for monitoring mode reconstruction. For purpose of illustration and not limitation, a total acquisition time can be 1.44 s, as described below. FIG. 9f depicts an exemplary monitoring mode reconstruction of the site in FIGS. 9b and 9e. The full-width half-maxima of the two exemplary centers from top to bottom can be 53 nm and 24 nm.

Wide field of view imaging can increase the speed of acquiring and resolving images of NV centers. For purpose of illustration and not limitation, an emCCD camera can be used for super-resolution imaging over a wide field of view, for example, a 35×35 µm² field of view. For example, a magnification of ~190× can project diffraction limited spots across 5 pixels on an exemplary emCCD, which can enhance the signal-to-noise ratio according to Eq. 8. For purpose of illustration and not limitation, a plurality of images, e.g. 90 images, can be captured at different microwave frequencies in a range, for example, microwave frequencies from 2.71 GHz to 2.88 GHz. Referring to FIG. 9a, a spot-finding technique can include selecting candidate fluorescence sites based on a fluorescence intensity threshold. For purpose of illustration but not limitation, fluorescence sites can be diffraction limited areas or an area that includes at least part of a wide field image. For example, a plurality of candidate fluorescence sites, e.g. 116 sites, can be selected based on the fluorescence intensity at each sites exceeds a threshold. Some or all of the candidate fluorescence sites can show fluorescence modulation due to the applied microwave field. For example, 95 out of 116 candidate sites can show fluorescence modulation due to the applied microwave field. Referring to FIG. 9b, the reconstructed image of a portion of the wide field of view can contain several diffraction-limited sites with multiple NV centers, and each NV center can be spectrally distinguishable. Referring to FIG. 9c, in some embodiments, the NV centers of a multi-spectral site can have partially overlapping Lorentzian resonances. These NV centers can be spatially resolved. Referring to FIG. 9d, the resulting reconstruction image of such a site with overlapping Lorentzian resonances is shown. For purpose of illustration, four NV centers can be identified. The localization of individual centers can range from 12 to 46 nm, and the localization can be indicated by the distributions as shown in the reconstructed image. In some embodiments, the color of each NV center depicted in a reconstruction can corresponds to a frequency in the microwave regime. This multicolor aspect can allow for multispectral labeling with sub-diffraction resolution. For purpose of illustration and not limitation, a total measurement time can be ~90 seconds over the entire 35×35 µm² field of view, and the NV centers can be localized with an average uncertainty of 27 nm and an uncertainty of down to 12 nm. A full ESR spectrum can be acquired across the entire field of view, and NV centers at a site containing more than four more NV centers can be resolved without additional images. For purpose of illustration, in some embodiments, a total acquisition time can be reduced and can correspond to a reduction in resolution, and the resolution can scale roughly as the inverse square root of the total exposure time.

In certain applications, such as molecular tracking, it can be desirable to focus on a sub-set of classes of the ESR spectrum to achieve higher acquisition rates. For example, images $I(x,y,\Omega_i)$ can be acquired at the microwave transition frequencies $\Omega_i$ of the emitters to be tracked, in addition to one off-resonant image, $I(x,y,\Omega_0)$. For purpose of illustration and not limitation, two NV centers can be resolved to be 55 nm apart with 25 nm resolution in an acquisition time of 1.44 seconds as shown in FIG. 9f. The resolution can be further improved by increasing ESR visibility. For example, several factors can impact visibility including but not limited to laser polarization, laser power, and the orientation of the microwave field. For purpose of illustration and not limitation, increasing laser power to ~250 kW/cm² can improve the average spatial resolution down to ~8 nm.

For purpose of illustration and not limitation, wide field measurements can be performed on a commercially available microscope, for example, a Zeiss Observor.Z1m outfitted with a commercially available photodetector such as a ProEM-512K CCD, using a 532 nm laser with 500 mW of power. Using a sample containing a nano-fabricated array, each 16 µm square pixel on the emCCD can be calibrated to correspond to 82 nm in size. To acquire the ESR spectrum for every NV center in the field of view, the emCCD can capture one frame, $I(x,y,\Omega)$ for each step in the microwave frequency sweep with an applied static magnetic field of ~55 G. Microwaves can be applied through a local wire located 15-30 µm from the sample surface. A commercially available piezoelectric mount such as a KC1-T-PZ can oscillate the defocused pump laser over a 1-2 µm area at ~110 Hz to reduce laser speckle on the sample. The vibrations of the sample can be minimized using a commercially available rigid sample holder, such as a closed-loop PI-545 piezoelectric stage with resolution less than 1 nm, and the camera can be liquid-cooled camera to avoid vibrations from a camera fan.

For purpose of illustration and not limitation, an Airy point spread function can be fit to difference plots, ΩI(x,y, Ω), using non-linear least square curve fitting tools, such as commercially available tools in MATLAB, by a symmetric Gaussian fitting with five free parameters: $\hat{I}_o$ for the total area under the Gaussian, $\hat{b}g$ for the background counts, $\hat{\sigma}$ for the standard deviation, and ($\hat{x}$, $\hat{y}$) for the center of the Gaussian function. Term P can be the length of the sample corresponding to each pixel on the CCD. The centers can be fit using the following equation:

$$\hat{I} = \hat{b}g + \frac{\pi \hat{I}_o \hat{\sigma}^2}{4}\left[\text{Erf}\left(\frac{x-\hat{x}+\frac{P}{2}}{\hat{\sigma}\sqrt{2}}\right) - \text{Erf}\left(\frac{x-\hat{x}-\frac{P}{2}}{\hat{\sigma}\sqrt{2}}\right)\right] \quad (9)$$

$$\left[\text{Erf}\left(\frac{y-\hat{y}+\frac{P}{2}}{\hat{\sigma}\sqrt{2}}\right) - \text{Erf}\left(\frac{y-\hat{y}-\frac{P}{2}}{\hat{\sigma}\sqrt{2}}\right)\right]$$

where Erf, the error function, can be used for binning of the Gaussian distribution due to a pixelated CD array.

Figure 10:
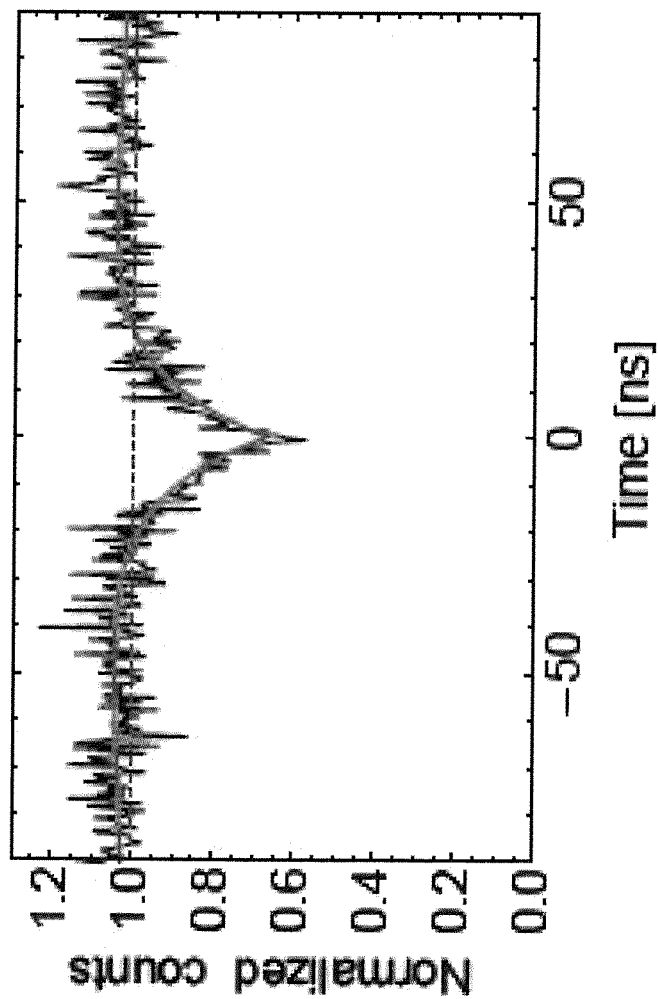
FIG. 10 is an exemplary normalized second order autocorrelation plot confirming the presence of no more than two emitters in the bulk sample shown in FIG. 8, in accordance with an embodiment of the disclosed subject matter.

FIG. 10 is an exemplary normalized second order auto-correlation plot confirming the presence of no more than two emitters in the bulk sample shown in FIG. 8, in accordance with an embodiment of the disclosed subject matter. For purpose of illustration and not limitation, the anti-bunching dip of the normalized second order auto-correlation ($g^2(\tau)$ =0.66) can confirm the presence of no more than two emitters accounting for background.

Figure 11:
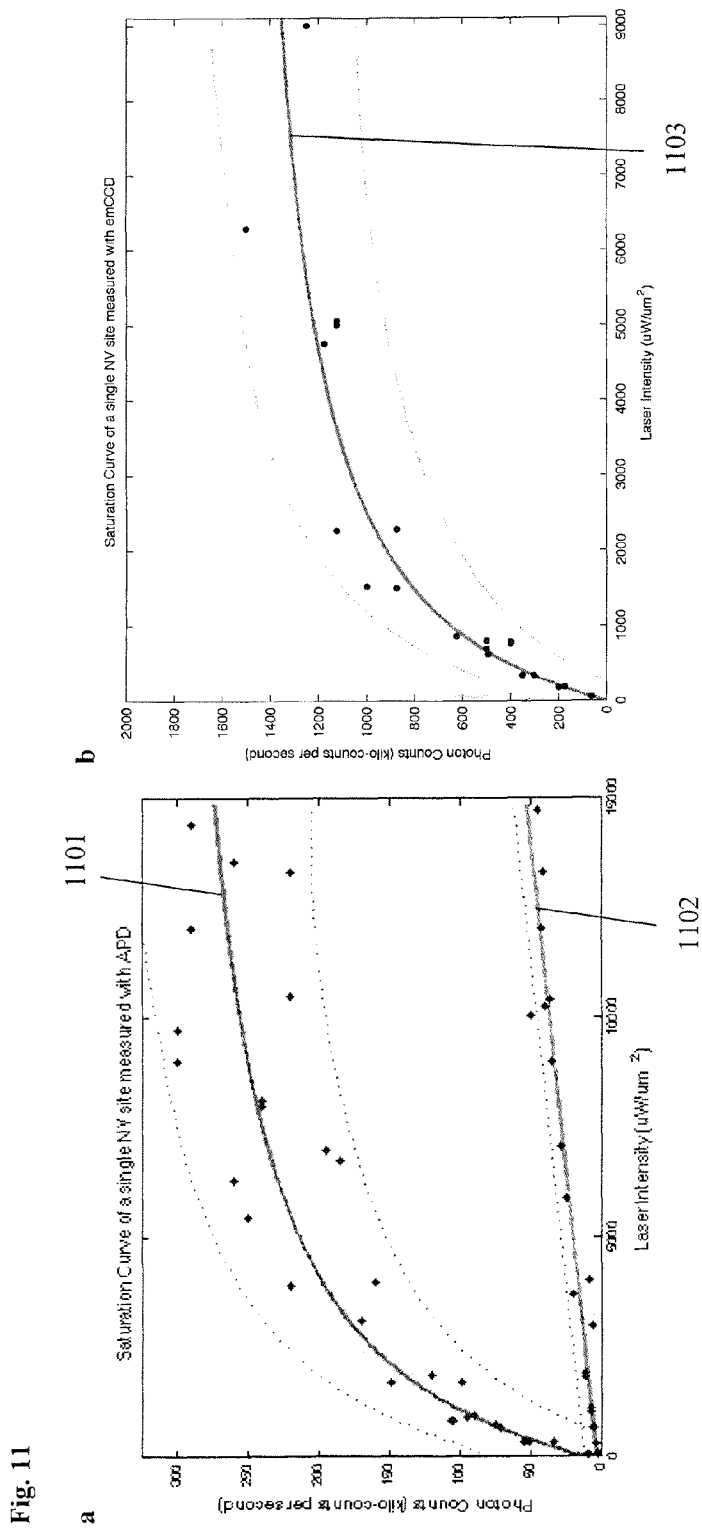
FIG. 11a shows an exemplary saturation curve for an avalanche photodiode (APD) in accordance with an embodiment of the disclosed subject matter.
FIG. 11b shows an exemplary saturation curve for a charge-coupled device (CCD) photodetector in accordance with an embodiment of the disclosed subject matter.

FIGS. 11a and 11b show the fluorescence of a single NV center saturating with respect to applied laser intensity using both an APD and an emCCD, where FIG. 11a shows an exemplary saturation curve for an APD in accordance with an embodiment of the disclosed subject matter, and FIG. 11b shows an exemplary saturation curve for an emCCD photodetector in accordance with an embodiment of the disclosed subject matter. For the exemplary APD saturation curve in FIG. 11a, the fitted curve 1101 can indicate a saturation count rate of 310 kilo-counts per second with a fitted curve 1102 that can show background linearly increasing with incident laser intensity. An exemplary saturation curve taken with the emCCD in FIG. 11b, a fitted curve 1103 can indicate a saturation fluorescence rate of ~1,600 kilo-counts per second. The photons count rate collected on the emCCD can be calculated as described below.

For example and not limitation, the equation for photon conversion calculation with emCCD can be given as:

$$G \times DU = (\gamma_{signal}\tau)QE \times M + (\gamma_D \tau) \quad (10)$$

where G is analog gain (electrons per ADU), DU is digital units on camera, $\gamma_{signal}$ is emission rate (Hz), $\tau$ is camera exposure time (sec), QE is quantum efficiency in converting a photon to an electron, M is the emCCD multiplication gain, and $\gamma_D$ is the dark count rate per pixel (Hz/pixel).

For purpose of illustration and not limitation, the spatial error as a function of laser power, exposure time, and number of emitters can be derived as follows. When using a CCD detector, the fundamental localization error can vary depending on the total magnification onto the camera. Light emitted from a point emitter and collected by a CCD detector can sacrifice spatial information due to the finite size of a pixel. If camera pixels can be assumed not to have read-out noise or dark counts, then increasing magnification can result in higher spatial resolution without any bound. However, because pixels can have a finite size and have some noise, a magnification can be balanced with spatial localization (see Eqns. 8 and 11). For example and not limitation, Eqn. 11 below can describe how magnification (~s/a) and background noise ($\sigma_{total}$) can affect the standard error on the mean of a Gaussian function fit to the emission profile of a single emitter.

$$\langle(\Delta x)^2\rangle = \frac{s^2 + a^2/12}{N} + \frac{8\pi s^4 \sigma_{total}^2}{a^2 N^2} \quad (11)$$

For purpose of illustration and not limitation, the emission properties of an exemplary NV emitter can be described as follows. The fluorescence rate from an NV emitter can depend on the intensity of the excitation laser, and can saturate at a peak rate, $R_\infty$, past an excitation intensity limit, $I_{sat}$ (Eqn. 11a). The signal, $N_{photons}$, can be the lack of photons counted from a single NV emitter when it is resonantly driven (Eqn. 11b), and the background noise, $\sigma_{total}$, of this emitter can depend upon the number of other emitters within the same diffraction volume that are not being resonantly addressed, assuming a shot-noise limit (Eqn. 11c). The lack of collected photons can be encapsulated by the contrast of the electron spin resonance measurement, C(I), which can reach a peak of around 15-20% and can be dependent on the incident laser power. The number of photons collected by the CCD also can depend on the system's total collection efficiency, $\eta$, and the exposure time, $\tau$. The total background noise can depend on the number of total emitters, m, in the diffraction volume, and more emitters can correspond to a decrease of the contrast compared with the background counts. Other contributions to background noise can include but are not limited to background fluorescence, which may increase with the pump laser intensity and can be parameterized by $\alpha$, and a constant background fluorescence, $\beta$.

$$C(I) = \Theta \frac{\Omega_T^2}{\Omega_\tau^2 + \Gamma_p^\infty \Gamma_c^\infty \left(\frac{s}{1+s}\right)^2}, \quad (11a)$$

$$\Gamma_{single}(I) = \frac{R_\infty I}{I_{sat} + I}, \quad (11b)$$

$$N_{photons}(I, \tau) = C(I)\eta\tau\Gamma_{single}(I). \quad (11c)$$

$$\sigma_{total}(m, I) = \sqrt{\eta\tau\Gamma_{single}(I)((m-1) + (1 - C(I))) + \alpha I + \beta}. \quad (11d)$$

Substitution of Eqns. 11a-11d into Eqn. 11 and after a few steps of algebra can give the standard error in localizing the mean of a Gaussian function as follows:

$$\langle(\Delta x)^2\rangle = \frac{s^2 + a^2/12}{N} + \frac{8\pi s^4 \sigma_{total}^2}{a^2 N^2}, \quad (12a)$$

$$= \frac{s^2}{N_{photons}}\left\{1 + \frac{1}{12}\left(\frac{a}{s}\right)^2 + \frac{8\pi}{\left(\frac{a}{s}\right)^2}\frac{\sigma_{total}^2}{N}\right\}, \quad (12b)$$

$$= \frac{s^2}{N_{photons}} \quad (12c)$$

$$\left\{1 + \frac{1}{12}\left(\frac{a}{s}\right)^2 + \frac{8\pi}{\left(\frac{a}{s}\right)^2}\frac{\frac{N_{photons}}{C(I)}(m-1+1-C(I)) + \alpha I + \beta}{N_{photons}}\right\},$$

$$= \frac{s^2}{N_{photons}} \left\{ 1 + \frac{1}{12}\left(\frac{a}{s}\right)^2 + \frac{8\pi}{\left(\frac{a}{s}\right)^2} \frac{m - C(I)}{C(I)} \right\} + O\left(\frac{1}{N_{photons}^2}\right). \quad (12d)$$

Figure 12:
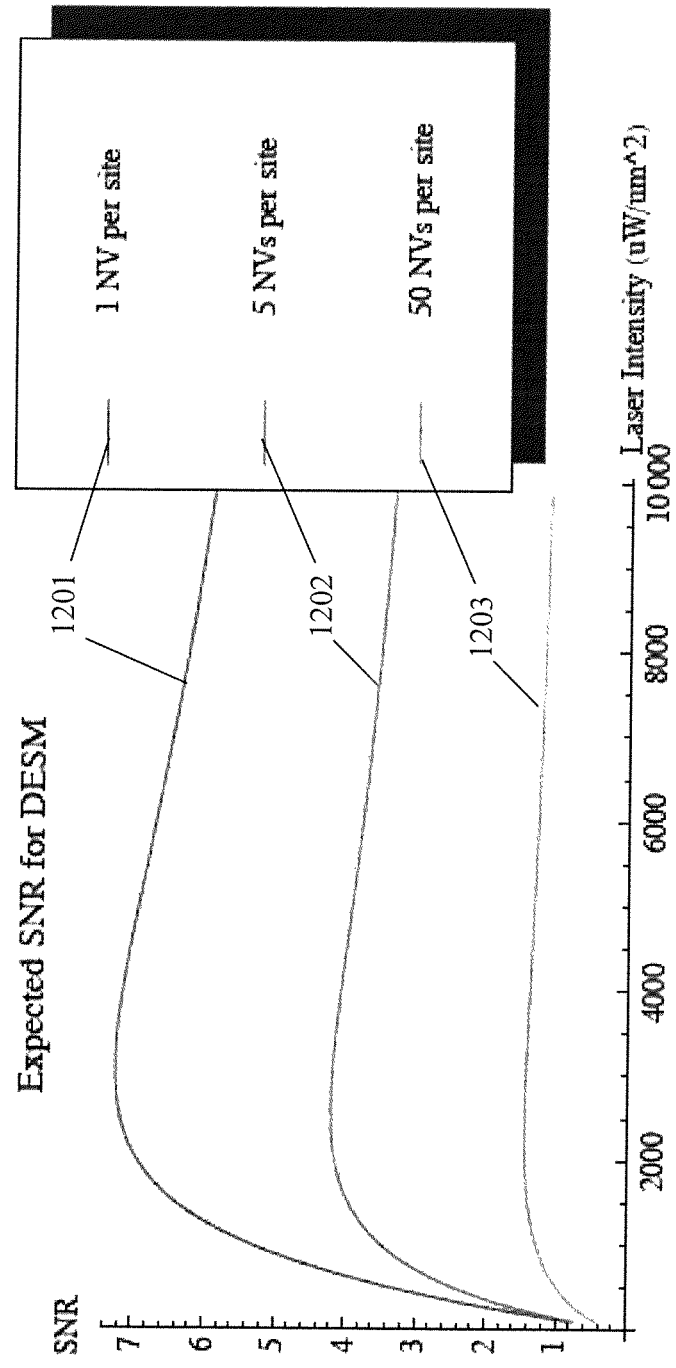
FIG. 12 illustrates an exemplary theoretical signal-to-noise ratio for resolving emitters with an emCCD photodetector in accordance with an embodiment of the disclosed subject matter.

FIG. 12 illustrates an exemplary theoretical signal-to-noise ratio for resolving emitters with an emCCD photodetector in accordance with an embodiment of the disclosed subject matter. For purpose of illustration and not limitation, the signal can be considered to be the contrast, C(I), multiplied by the fluorescence from a single NV collected at the shot-noise-limit. For example and not limitation, the equations above can be used to plot the signal-to-noise ratio as a function of laser intensity for m=1, 5 and 50 emitters per diffraction limited spot (1201, 1202, 1203, respectively). For example, to resolve 5 emitters in a site, it can be estimated that up to 200 kW/cm$^2$ or more of laser intensity can be used.

Figure 13:
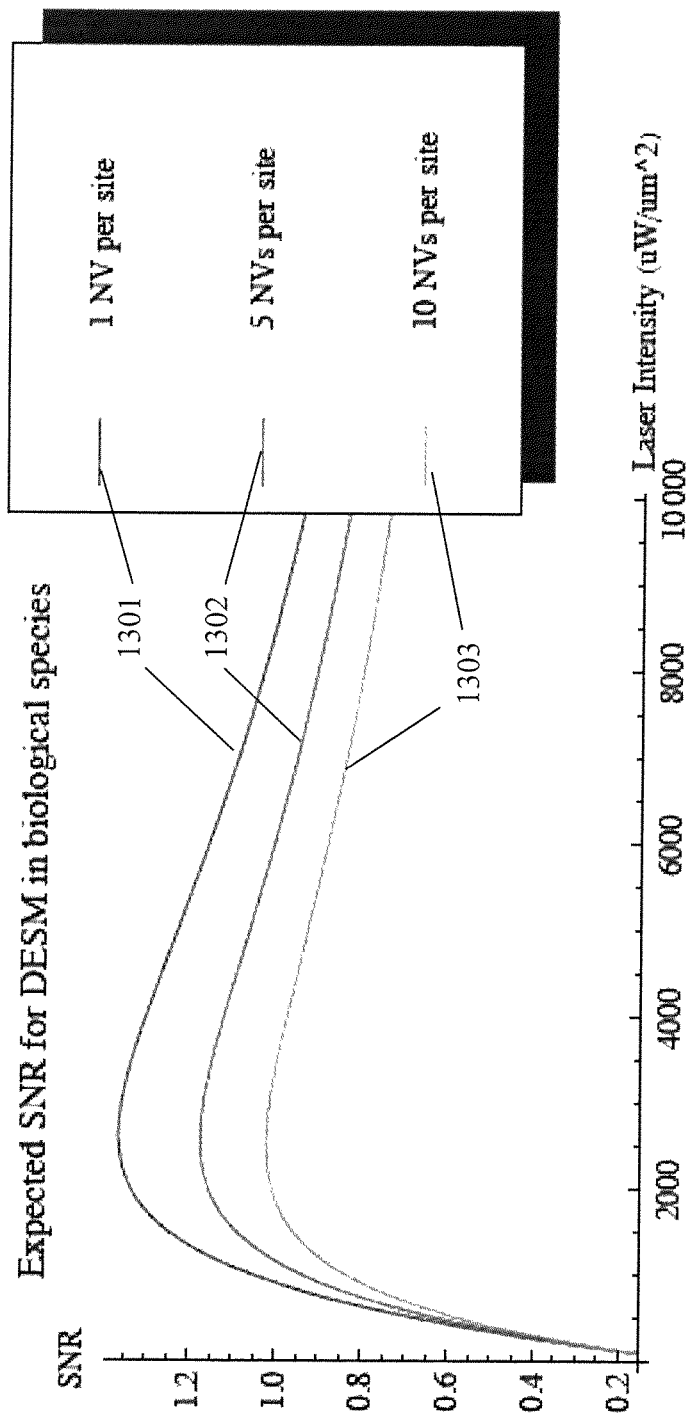
FIG. 13 illustrates an exemplary expected signal-to-noise ratio for resolving emitters in a biological species in accordance with an embodiment of the disclosed subject matter.

FIG. 13 illustrates an exemplary expected signal-to-noise ratio for resolving emitters in a biological species in accordance with an embodiment of the disclosed subject matter. For example and not limitation, the number of resolvable emitters can be estimated by assuming five times more background counts and five times less collected photon counts for biologically ingested nanodiamonds with NV centers. For purpose of illustration and not limitation, nanodiamonds can be internalized by HeLa cells and can have little rotational diffusion. For example, 45 nm-sized nanodiamonds internalized by HeLa cells can have an estimated angular rotation of less than 10 degrees over several hours.

To account for the increased background and lower collection efficiency for imaging in biological samples, Eqns. 7, 8, and 12a-d can be used. The fluorescence rate from single NV centers can be ~100 kcps, which can be compared with the peak detected fluorescence detected from a stable NV in nanodiamond of ~500 kcps. Assuming the collected fluorescence rate from biologically ingested nanodiamonds can decrease by a factor of 5 ($R_\infty \rightarrow R_\infty/5$) and the background counts can increase by a factor of 5 ($\alpha \rightarrow \alpha \times 5$), then the estimated exposure time can increase by a factor of ~22 to achieve the same SNR. In FIG. 13, it can be estimated that up to 10 unique centers per diffraction limited spot can be addressed for biologically ingested nanodiamonds.

Figure 14:
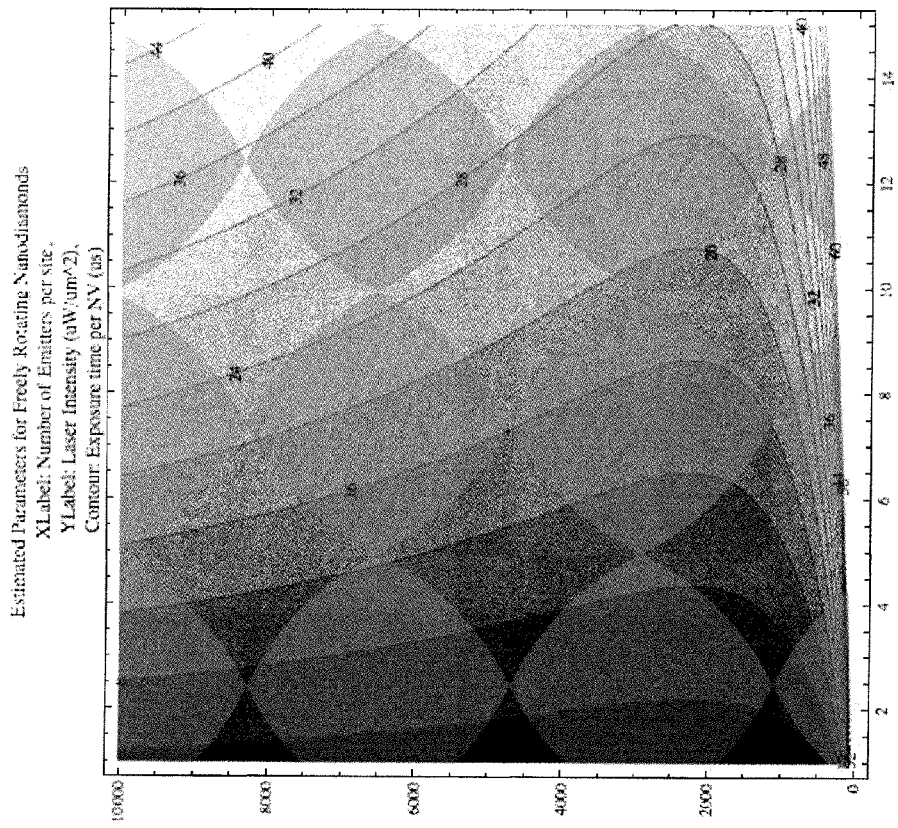
FIG. 14 illustrates an exemplary estimated number of resolvable centers from freely rotating nanodiamonds in accordance with some embodiments of the disclosed subject matter.

FIG. 14 illustrates an exemplary estimated number of resolvable centers from freely rotating nanodiamonds in accordance with some embodiments of the disclosed subject matter. The greater the number of resolved emitters (X-axis), the greater the exposure time (contour, µs) can be used per emitter for an ODMR signal with a unity SNR. For purpose of illustration and not limitation, freely rotating nanodiamonds can be expected to rotate at a rate of ~1 rad$^2$/ms for 50 nm nanodiamonds. Using a combination of a solid immersion lens and a reflective top surface can increase the collection efficiency enough to collect 5-10 times more fluorescence from a single NV. As such, a unity SNR in the ODMR contrast can be achieved within ~20 µs of exposure time, during which time the nanodiamond can be expected to rotate by 8 degrees. With such angular resolution, up to ~10 NV orientations can be uniquely addressable.

The DESM techniques described herein can pinpoint the position of NV centers below the diffraction limit with resolution comparable to super-resolution stochastic methods. Certain techniques can employ multiple optically distinguishable emitters for super-resolution single-molecule tracking, and can offer a lesser number of spectral channels for multispectral fluorescence microscopy than DESM. DESM can be used to distinguish up to 55 or more different emitters in a spot. Pulsed electron spin techniques can improve the contrast ratio and reduce the effective linewidth, which can result in more uniquely resolvable centers within a diffraction volume. Additionally or alternatively, higher quality nanodiamonds with long spin-coherence times can be used for improving super-resolution images. Additionally, super-resolution imaging using fluorescent nanodiamonds can have advantages compared to certain techniques using fluorescent markers for biological applications, including but not limited to photostability, cytocompatibility, and high-resolution magnetic and electric field sensitivity. DESM also can allow for detecting a high fluorescence intensity exceeding 1.5×10$^6$ photons per second for a single NV center at saturation. In biological applications, the rotation of nanodiamonds and increased background can reduce the number of resolvable centers. For freely rotating nanodiamonds in an aqueous environment, ~10 orientations can be resolved with a rotation rate of 1 rad$^2$/ms with a tenfold improvement in collection efficiency. Additionally or alternatively, biologically ingested nanodiamonds can undergo relatively little rotational diffusion over several hours. Due to increased background, the number of resolvable emitters can be estimated to be ~10 orientations. The techniques described herein can achieve a frame rate of up to 0.7 Hz, sub-wavelength localization down to 12 nm, and ability for uninterrupted monitoring of individual emitters.

The techniques described herein can be implemented on other emitters exhibiting ODMR such as the silicon defect center in silicon carbide, and single organic molecules.

The presently disclosed subject matter is not to be limited in scope by the specific embodiments herein. Indeed, various modifications of the disclosed subject matter in addition to those described herein will become apparent to those skilled in the art from the foregoing description and the accompanying figures. Such modifications are intended to fall within the scope of the appended claims.

The invention claimed is:

1. A method for resolving at least one nitrogen vacancy center, comprising:
    providing at least one diamond structure with one or more nitrogen vacancy centers within a focal location, wherein the focal location is a wide field of view, each nitrogen vacancy center being in either a dark state or a bright state;
    applying a magnetic field across the at least one diamond structure;
    optically exciting the one or more nitrogen vacancy centers;
    switching at least one nitrogen vacancy center from the dark state to the bright state or from the bright state to the dark state by applying at least one microwave pulse to the one or more nitrogen vacancy centers;
    detecting a fluorescent response of each nitrogen vacancy center; and
    resolving at least one of the nitrogen vacancy centers based on the fluorescent response of each nitrogen vacancy center, the fluorescent response of each nitrogen vacancy center corresponding to its orientation relative to the magnetic field.

2. The method of claim 1, wherein the optically exciting includes directing a continuous wave of pump light at approximately 532 nm to the nitrogen vacancy center.

3. The method of claim 1, wherein the optically exciting includes applying a pulse of pump light at approximately 532 nm to the nitrogen vacancy center prior to applying the at least one microwave pulse, and applying a pulse of pump light at approximately 532 nm to the nitrogen vacancy center subsequent to applying the at least one microwave pulse.

4. The method of claim 1, wherein the providing at least one diamond structure with one or more nitrogen vacancy centers further comprises providing a plurality of nitrogen vacancy centers, at least some having differing orientations with respect to the magnetic field, whereby a spin sublevel of each nitrogen vacancy center experiences a Zeeman splitting corresponding to the orientation of the nitrogen vacancy center with respect to the magnetic field.

5. The method of claim 4, wherein applying at least one microwave pulse further comprises tuning a first microwave pulse to a field splitting frequency of a first one of the nitrogen vacancy centers, thereby modulating the fluorescent response of the first one of the nitrogen vacancy centers.

6. The method of claim 5, wherein applying at least one microwave pulse further comprises tuning at least a second microwave pulse to a field splitting frequency of a second one of the nitrogen vacancy centers, thereby modulating the fluorescent response of the second one of the nitrogen vacancy centers.

7. The method of claim 6, wherein applying at least one microwave pulse further comprises:
    applying the first microwave pulse at a first frequency, the first frequency tuned to the field splitting frequency of the first one of the nitrogen vacancy centers;
    applying the second microwave pulse at a second frequency, the second frequency tuned to the field splitting frequency of the second one of the nitrogen vacancy centers; and
    applying at least a third microwave pulse at a third frequency, the third frequency tuned a frequency not corresponding to a field splitting frequency of either the first or the second one of the nitrogen vacancy centers.

8. The method of claim 6, wherein detecting the fluorescent response of each nitrogen vacancy center further comprises:
    generating a first intensity plot of a first fluorescent response corresponding to the first frequency;
    generating a second intensity plot of a second fluorescent response corresponding to the second frequency; and
    generating at least a third intensity plot of a third fluorescent response corresponding to the third frequency.

9. The method of claim 8, wherein resolving the at least one nitrogen vacancy center includes determining the position of the first one of the nitrogen vacancy centers by subtracting the first and third intensity plots from the second intensity plot.

10. The method of claim 1, wherein applying at least one microwave pulse further includes continuously varying a frequency of a microwave emission.

11. The method of claim 1, wherein the switching at least one nitrogen vacancy center and the detecting a florescent response further comprises applying a plurality of microwave pulses and detecting a plurality of fluorescent responses, corresponding to the plurality of microwave pulses, to obtain a full electron spin resonance spectrum for a plurality of locations of a sample; and wherein resolving at least one nitrogen vacancy center further comprises:
    fitting the electronic spin resonance spectrum with a sum of Lorentzian dips;
    generating an intensity map for the nitrogen vacancy center using contrasts from the fitted electron spin resonance spectrum.

12. The method of claim 11, wherein at least one of the Lorentzian dips at least partially overlaps at least one other of the Lorentzian dips.

13. The method of claim 1, wherein the focal location contains a plurality of diffraction-limited areas.

14. The method of claim 1, wherein the focal location includes at least one diffraction-limited area selected from the wide field of view, the selected at least one diffraction-limited area having a fluorescent response with an intensity above a threshold.

15. The method of claim 1, wherein the focal location includes a confocal scan area.

16. The method of claim 1, further comprising:
    providing at least one fluorophore having an emission spectrum at least partially overlapping with an emission spectrum of the one or more nitrogen vacancy centers, wherein a fluorescent response of one of the nitrogen vacancy centers optically excites the fluorophore if the one of the nitrogen vacancy centers is within a threshold distance of fluorophore; and
    detecting a fluorescent response of the fluorophore corresponding to the optical excitation of the one of the nitrogen vacancy centers.

17. The method of claim 16, further comprising determining a distance of one of the nitrogen vacancy centers from the fluorophore based on at least the fluorescent response of the one of the nitrogen vacancy centers and the fluorescent response of the fluorophore.

18. The method of claim 16, further comprising determining an orientation of a magnetic dipole of a molecule, the fluorophore coupled to the molecule, based on at least the fluorescent response of the one of the nitrogen vacancy centers and the fluorescent response of the fluorophore.

19. The method of claim 1, wherein the at least one diamond structure is exposed to an environment, wherein applying at least one microwave pulse includes applying two or more microwave pulses, each microwave pulse having a different frequency, and wherein detecting the fluorescent response of each nitrogen vacancy center includes detecting a fluorescent response corresponding to each microwave pulse, the method further comprising determining, based on the fluorescent response of each nitrogen vacancy center, a characteristic of the environment.

20. The method of claim 19, wherein the characteristic of the environment includes local magnetic field, local electric field, or pH.

21. The method of claim 1, further comprising determining the location of a particle corresponding to the resolved at least one of the nitrogen vacancy centers.

22. A system for resolving at least one nitrogen vacancy center within a focal location using an applied magnetic field, wherein the focal location is a wide field of flew, comprising:
    a light source, operatively configured to excite the at least one nitrogen vacancy center in the presence of the applied magnetic field, thereby inducing the at least one nitrogen vacancy center to produce a fluorescent response;
    a photodetector arranged to detect the fluorescent response, if any;
    a tunable microwave emitter arranged to apply at least one microwave pulse to the at least one nitrogen vacancy center; and
    a control unit, coupled to the photodetector and the tunable microwave emitter, configured to adjust the frequency of the tunable microwave emitter, and configured to resolve the at least one nitrogen vacancy center based on the fluorescent response, the fluorescent response corresponding to its orientation relative to the magnetic field.

23. The system of claim 22, wherein the photodetector includes an array of pixels, and wherein the photodetector is further arranged to detect an intensity map of the fluorescent response across the array of pixels.

24. The system of claim 23, further comprising far-field optics to direct the fluorescent response to the photodetector.

25. The system of claim 24, wherein the focal location includes a plurality of diffraction-limited areas, and wherein the array of pixels corresponds to at least the diffraction-limited areas.

26. The system of claim 25, wherein the control unit is further configured to:
adjust the frequency of the tunable microwave emitter to a first frequency, the first frequency corresponding to an $m_s=+1$ spin sublevel field splitting frequency of the at least one nitrogen vacancy center;
adjust the frequency of the tunable microwave emitter to a second frequency, the second frequency corresponding to a zero field splitting frequency of the at least one nitrogen vacancy center; and
adjust the frequency of the tunable microwave emitter to at least a third frequency, the third frequency corresponding to an $m_s=-1$ spin sublevel field splitting frequency of the at least one nitrogen vacancy center.

27. The system of claim 26, wherein the control unit is further configured to:
receive from the photodetector a first intensity plot of a first fluorescent response corresponding to the first frequency;
receive from the photodetector a second intensity plot of a second fluorescent response corresponding to the second frequency; and
receive from the photodetector at least a third intensity plot of a third fluorescent response corresponding to the third frequency; and
wherein the first, second, and third intensity plots include a measurement of intensity of the fluorescent response over the array of pixels.

28. The system of claim 27, wherein the control unit is further configured to resolve the at least one nitrogen vacancy center based on by subtracting the first and third intensity plots from the second intensity plot.

29. The system of claim 24, wherein the array of pixels corresponds to at least the wide field of view.

30. The system of claim 24, wherein the focal location includes at least one diffraction-limited area selected from the wide field of view, the selected at least one diffraction-limited area having a fluorescent response with an intensity above a threshold, and wherein the array of pixels corresponds to at least the wide field of view.

31. The method of claim 23, wherein the focal location includes a confocal scan area, and wherein the array of pixels corresponds to at least the confocal scan area.

32. The system of claim 22, wherein the light source includes a laser adapted to continuously irradiate the at least one nitrogen vacancy center with approximately 532 nm light.

33. The system of claim 22, wherein the light source is coupled to the control unit, and wherein the light source includes a laser adapted to apply a pulse of pump light at approximately 532 nm to the at least one nitrogen vacancy center prior to application of the at least one microwave pulse, and adapted to apply a pulse of pump light at approximately 532 nm to the nitrogen vacancy center subsequent to application of the at least one microwave pulse.

34. A method for resolving at least one deterministic emitter, comprising:
providing at least one structure with one or more deterministic emitters within a focal location, wherein the focal location is a wide field of view, each deterministic emitter being in either a dark state or a bright state;
applying a magnetic field across the at least one structure;
optically exciting the one or more deterministic emitters;
switching at least one deterministic emitter from the dark state to the bright state or from the bright state to the dark state by applying at least one microwave pulse to the one or more deterministic emitters;
detecting a fluorescent response of each deterministic emitter; and
resolving at least one of the deterministic emitters based on the fluorescent response of each deterministic emitter, the fluorescent response of each deterministic emitter corresponding to its orientation relative to the magnetic field.

35. The method of claim 34, wherein the at least one structure comprises at least one diamond structure and the one or more deterministic emitters comprises one or more nitrogen vacancy centers.

36. The method of claim 34, wherein the at least one structure comprises at least one silicon carbide structure and the one or more deterministic emitters comprises one or more silicon defects.

* * * * *